US009005888B2

(12) United States Patent
Antes et al.

(10) Patent No.: US 9,005,888 B2
(45) Date of Patent: Apr. 14, 2015

(54) METHODS FOR MICROVESICLE ISOLATION AND SELECTIVE REMOVAL

(71) Applicant: System Biosciences, LLC, Mountain View, CA (US)

(72) Inventors: Travis John Antes, Sunnyvale, CA (US); Kevin Kwei, Mountain View, CA (US); Fangting Wu, Mountain View, CA (US)

(73) Assignee: System Biosciences, LLC, Mountain View, CA (US)

( * ) Notice: Subject to any disclaimer, the term of this patent is extended or adjusted under 35 U.S.C. 154(b) by 0 days.

(21) Appl. No.: 13/918,260

(22) Filed: Jun. 14, 2013

(65) Prior Publication Data
US 2013/0337440 A1 Dec. 19, 2013

Related U.S. Application Data

(60) Provisional application No. 61/659,628, filed on Jun. 14, 2012, provisional application No. 61/800,213, filed on Mar. 15, 2013.

(51) Int. Cl.
*C12Q 1/00* (2006.01)
*C12Q 1/02* (2006.01)
*G01N 1/34* (2006.01)
*C12Q 1/68* (2006.01)
*G01N 33/50* (2006.01)
*G01N 33/52* (2006.01)
*C12M 1/00* (2006.01)

(52) U.S. Cl.
CPC ............... *G01N 1/34* (2013.01); *C12Q 1/6895* (2013.01); *G01N 33/5002* (2013.01); *G01N 33/52* (2013.01); *C12M 29/26* (2013.01)

(58) Field of Classification Search
USPC ....................................... 435/4, 29
See application file for complete search history.

(56) References Cited

U.S. PATENT DOCUMENTS

| 7,166,443 | B2 | 1/2007 | Walker et al. | |
|---|---|---|---|---|
| 7,875,446 | B2 | 1/2011 | Kang et al. | |
| 8,021,847 | B2 | 9/2011 | Pietrzkowski | |
| 2010/0075315 | A1 | 3/2010 | Pietrzkowski | |
| 2010/0305303 | A1 | 12/2010 | Xu | |
| 2013/0273544 | A1 | 10/2013 | Vlassov et al. | |
| 2013/0337440 | A1* | 12/2013 | Antes et al. | 435/6.1 |
| 2014/0178888 | A1 | 6/2014 | Vlassov et al. | |

FOREIGN PATENT DOCUMENTS

| EP | 2522689 A1 | 11/2012 |
|---|---|---|
| WO | 2012/054975 | 5/2012 |
| WO | 2013/158203 | 10/2013 |

OTHER PUBLICATIONS

Adams, "Concentration of Epstein-Barr virus from cell culture fluids with polyethylene glycol," J. Gen. Virol., 20: 391-394 (1973).
Cheruvanky et al., "Rapid isolation of urinary exosomal biomarkers using a nanomembrane ultrafiltration concentrator." J. Physiol. Renal Physiol., 292: 1657-1661 (2007).
Kosaka et al., "microRNA as a new immune-regulatory agent in breast milk" Silence 3:1-7 (2010).
Mitchell et al., "Circulating microRNAs as stable blood-based markers for cancer detection," PNAS 105(30): 10513-10518 (2008).
Mittelbrunn and Sanchez-Madrid, "Intercellular communication: diverse structures for exchange of genetic information" Nature Reviews Molecular and Cellular Biology 13: 328-335 (2012).
Palanisamy et al., "Nanostructural and Transcriptomic Analyses of Human Saliva Derived Exosomes," PLoS One 5 (2010), e8577.
Thery et al., "Exosomes: Composition, Biogenesis and Function," Nat. Rev. Immunol. 2: 569-579 (2002).
Thery et al., "Isolation and Characterization of Exosomes from Cell Culture Supernatants and Biological Fluids," Current Protocols in Cell Biol., Chapter 3: 3.22.1-3.22.29 (2006).
Valadi et al., "Exosome-mediated transfer of mRNAs and microRNAs is a novel mechanism of genetic exchange between cells," Nat. Cell. Biol. 9(6): 654-659 (2007).
Wang et al., "Export of microRNAs and microRNA-protective protein by mammalian cells" Nucleic Acids Res., 38: 7248-7259 (2010).
Yamamoto et al., "Rapid bacteriophage sedimentation in the presence of polyethylene glycol and its application to large-scale virus purification," Virology 40: 734-744 (1970).
System Biosciences, Inc., "Exosome Research," 8 pgs, published approximately Mar. 2012, retrieved from <http://www.systembio.com/downloads/Exosome_mini-brochure_2014.pdf>; [retrieved on May 8, 2014].
Akbas et al., "Analysis of serum micro-RNAs as potential biomarker in chronic obstructive pulmonary disease," Exp Lung Res. 38(6):286-294 (Aug. 2012).
Alvarez et al., "Comparison of protein, microRNA, and mRNA yields using different methods of urinary exosome isolation for the discovery of kidney disease biomarkers," Kidney Int. (Jul. 11, 2012); doi: 10.1038/ki.2012.256.
Bala et al., "Circulating microRNAs in exosomes indicate hepatocyte injury and inflammation in alcoholic, drug-induced and inflammatory liver diseases," Hepatology (Jun. 9, 2012). doi: 10.1002/hep.25873.

(Continued)

*Primary Examiner* — Susan Hanley
*Assistant Examiner* — Paul Martin
(74) *Attorney, Agent, or Firm* — Dergosits & Noah LLP

(57) ABSTRACT

The invention relates to compositions and methods for isolation of microvesicles produced by mammalian cells. These microvesicles, known as extracellular microvesicles or circulating microvesicles, are isolated from sample materials such as body fluids, or from cell culture media that has been used to culture and maintain mammalian cells in vitro. The isolation of microvesicles as described herein results in purification and concentration of the microvesicles.

The invention also provides related methods for producing blood serum and/or blood plasma that is free of detectable microvesicles, largely depleted of microvesicles, or has reduced concentration of microvesicles compared to the blood serum or blood plasma starting material (collectively termed "microvesicle-depleted"). The generation of microvesicle-depleted blood serum or plasma is critical for use in experimental systems where it is desirable to use a cell culture media that does not contain endogenous microvesicles, or has been depleted of endogenous microvesicles, from the source material.

23 Claims, 12 Drawing Sheets

(56) References Cited

OTHER PUBLICATIONS

Bhatnagar et al., "Exosomes released from macrophages infected with intracellular pathogens stimulate a proinflammatory response in vitro and in vivo," Blood vol. 110, No. 9:3234-3244 (2007).
Camussi et al., "Exosome/microvesicle-mediated epigenetic reprogramming of cells," Am J Cancer Res 1(1):98-110 (Epub Oct. 22, 2010; published Jan. 1, 2011).
Chang et al., "Secretomic analysis identifies A1AT as a required protein in cancer cell migration, invasion, and pericellular fibronectin assembly for facilitating lung colonization of lung adenocarcinoma cells," Mol Cell Proteomics (Aug. 15, 2012).
Chen et al., "Cardiac progenitor-derived exosomes protect ischemic myocardium from acute ischemia/reperfusion injury," Biochem. Biophys. Res. Commun. 431: p. 566-571 (epub Jan. 11, 2013).
Dragovic et al., "Sizing and phenotyping of cellular vesicles using Nanoparticle Tracking Analysis," Nanomedicine: Nanotechnology, Biology and Medicine (2011), doi:10.1016/j.nano.2011.04.003.
Epple et al., "Medulloblastoma Exosome Proteomics Yield Functional Roles for Extracellular Vesicles," PLoS One 7 (7): e42064 (2012). doi:10.1371/journal.pone.0042064.
Kadiu et al., "Biochemical and Biologic Characterization of Exosomes and Microvesicles as Facilitators of HIV-1 Infection in Macrophages," J Immunol. (ePub Jun. 18, 2012).
Hoon-Lee et al., "Review: Microvesicles as mediators of intercellular communication in cancer—the emerging science of cellular 'debris'," Seminars in Immunopathology 33(5):455-467 (Sep. 2011; Epub Feb. 12, 2011) DOI:10.1007/s00281-011-0250-3.
Lewis and Metcalf, Applied and Environmental Microbiology, vol. 54, No. 8, p. 1983-1988 (Aug. 1988).
Mathivanan and Simpson, "Exosomes: extracellular organelles important in intercellular communication," J. Proteomics 73(10):1907-1920 (2010).
Merz et al., "Biochemical and Morphological Properties of Hepatitis C Virus Particles and Determination of Their , Lipidome" Jour. Biol. Chemistry vol. 286, No. 4, p. 3018-3032 (Jan. 28, 2011).
Sakwe et al., "Fetuin-A (alpha-2HS-Glycoprotein) Is a Major Serum Adhesive Protein That Mediates Growth Signaling in Breast Tumor Cells," J Biol Chem. 285(53):41827-41835 (2010).
Simpson and Mathivanan (2012), "Extracellular Microvesicles: The Need for Internationally Recognized Nomenclature and Stringent Purification Criteria". J Proteomics Bioinform (2). doi:10.4172/jpb.10000e10.
Tauro et al., "Comparison of ultracentrifugation, density gradient separation, and immunoaffinity capture methods for isolating human colon cancer cell line LIM1863-derived exosomes," Methods 56(2):293-304 (print Feb. 2012, Epub Jan. 21, 2012), doi:10.1016/j.ymeth.2012.01.002.
Taylor et al., "Exosome Isolation for Proteomic Analyses and RNA Profiling," Serum/Plasma Proteomics, Methods in Molecular Biology, vol. 728, Part 4, Chapter 15, p. 235-246 (2011).
Umezu et al., "Leukemia cell to endothelial cell communication via exosomal miRNAs," Oncogene (Jul. 16, 2012); doi: 10.1038/onc.2012.295.
Van der Pol et al., "Optical and non-optical methods for detection and characterization of microparticles and exosomes," Journal of Thrombosis and Haemostasis (2010), doi: 10.1111/j.1538-7836.2010.04074.x.
Vlassov et al., "Exosomes: Current knowledge of their composition, biological functions, and diagnostic and therapeutic potentials," Biochemica et Biophysica Acta 1820: p. 940-948. (Apr. 1, 2012).
Watson et al., "Fetuin-A triggers the secretion of a novel set of exosomes in detached tumor cells that mediate their adhesion and spreading," FEBS Letters (Aug. 8, 2012).
Xiao et al., "Identifying mRNA, MicroRNA and Protein Profiles of Melanoma Exosomes," PLoS One, vol. 7(10); (Oct. 2012).
"Total Exosome Isolation (from Serum)," LifeTechnologies™, catalog No. 4478360. Two pages, (2012).
"Total Exosome Isolation (from Cell Culture Media)," LifeTechnologies™, catalog No. 4478359. Two pages, (2012).
LifeTechnologies™ (Invitrogen) "Total Exosome RNA and Protein Isolation Kit; for isolation of RNA and protein from exosomes," User Manual, Catalog No. 4478545, Revision Date Jun. 28, 2012; Publication No. MAN0006962. 40 pages.

"ExoQuick™ Exosome Precipitation Solution," User Manual, Catalog Nos. EXOQ5A-1 and EXOQ20A-1, manufactured by System Biosciences, Inc. (SBI; Mountain View, California). Manual Ver. Feb. 22, 2013. 11 pages. ExoQuick™ offered for sale in Apr. 2010.
"ExoQuick-TC™ Exosome Precipitation Solution," User Manual, Catalog Nos. EXOTCxxA-1, manufactured by System Biosciences, Inc. (SBI; Mountain View, California). Manual Ver. Aug. 5, 2011. 10 pages. ExoQuick-TC™ offered for sale in Aug. 2011.
ExoQuick-TC™ Exosome precipitation, product sheet; two pages. Retrieved from www.systembio.com in Jul. 2013.
"Exo-FBS™ Exosome-depleted FBS," User Manual, Catalog Nos. EXO-FBSxxx. Manual dated Aug. 7, 2012. 17 pages. Exo-FBS™ product offered for sale Sep. 10, 2012.
"Exo-FBS™ Exosome-depleted FBS," Product Sheet (two pages). Retrieved from www.systembio.com in Jul. 2013.
"PEG-it™ Virus Precipitation Solution (5x)," User Manual, Catalog No. LV810A-1/LV825A-1, by System Biosciences, Inc. (Mountain View, California),(2010).
Communication "Study and Analysis of MicroRNAs in Exosomes." System Biosciences, Inc. (Mountain View, California), Dec. 2009. Nine pages.
Wu and Antes, "An exosome isolation system for serum-based cancer biomarker discovery," Proceedings of the 101st Annual Meeting of the American Association of Cancer Research (Washington, DC; Apr. 17-21, 2010), Abstract No. 3030, Poster Presentation Section 4; presentation made on Apr. 20, 2010. Published in Cancer Research, vol. 70, Issue 8, Supplement 1 (Apr. 15, 2010).
Exosomes and Microvesicles Conference, Orlando, Florida, Sep. 29 through Oct. 2, 2012. 38 pages. Presentation made on Sunday, Sep. 30, 2012.
Exosomes and Microvesicles Conference, Orlando, Florida, Sep. 29 through Oct. 2, 2012. Meeting Program (6 pages).
System Biosciences. "ExoQuick-TC Exosome Precipitation Solution." [User Manual Online] SystemBiosciences, LLC, version 4-2011-08-05, Aug. 5, 2011 [retrieved on Nov. 5, 2013 from www.biocat.com/bc/pdf/Manual_ExoTC_WEB.pdf; p. 3, protocol, steps 2, 4; p. 4, C, step 8; p. 5, Nanosight.
Vlassov, V et al. "Exosomes: current knowledge of their composition, biological functions, and diagnostic and therapeutic potentials." Biochimica et Biophysica Acta vol. 1820, pp. 940-948, Apr. 1, 2012.
Taylor, DD et al. "Exosome isolation for proteomic analyses and RNA profiling." Serum/Plasma Proteomics: Methods in Molecular Biology, vol. 728, pp. 235-246, Humana Press, 2011.
International Search Report and Written Opinion in corresponding patent application No. PCT/US13/45997 dated Nov. 22, 2013.
Xin et al., "Mir-133b Promotes Neural Plasticity and Functional Recovery after Treatment of Stroke with Multipotent Mesenchymal Stromal Cells in Rats Via Transfer of Exosome-Enriched Extracellular Particles," Stem Cells (epub Apr. 30, 2013) doi: 10.1002/stem.1409.
Wu et al. "An Exosome Isolation System for Serum and Biofluid-based Cancer Biomarker Discovery," poster presented at the 101st Annual Meeting of the American Association of Cancer Research, Washington, DC, on Apr. 20, 2010.
System Biosciences, Inc. (Mountain View, CA), "Bergen County Academy Uses ExoQuick-TC and CytoTracers," SBInsights, Issue No. 4, p. 7 (Jan. 2012). Retrieved from <www.systembio.com>.
System Biosciences, Inc. (Mountain View, CA), Press Releases and New Product Releases webpage, retrieved from <www.systembio.com>, accessed on Sep. 17, 2014.
System Biosciences, Inc. (Mountain View, CA), "One-step Exosome Isolation and Detection," Products Brochure, p. 13, retrieved from <www.systembio.com>, accessed on Sep. 17, 2014.
ExoQuick(TM) Exosome Precipitation Solution, User Manual, Catalog Nos. EXOQ5A-1 and EXOQ20A-1, manufactured by System Biosciences (SBI; Mountain View, CA). Manual Version 1, printed with the date Apr. 22, 2010.
ExoQuick(TM) Exosome Precipitation Solution, User Manual, Catalog Nos. EXOQ5A-1 and EXOQ20A-1, manufactured by System Biosciences (SBI; Mountain View, CA). Manual Version 2, printed with the date Jul. 2, 2010.
ExoQuick(TM) Exosome Precipitation Solution, User Manual, Catalog Nos. EXOQ5A-1 and EXOQ20A-1, manufactured by System Biosciences (SBI; Mountain View, CA). Manual Version 4, printed with the date Jul. 11, 2011.

* cited by examiner

METHODS FOR MICROVESICLE ISOLATION AND SELECTIVE REMOVAL

CROSS-REFERENCE TO RELATED APPLICATIONS

This application claims the benefit of the U.S. Provisional Application Ser. No. 61/659,628, filed Jun. 14, 2012, and Ser. No. 61/800,213, filed Mar. 15, 2013.

FIELD OF THE INVENTION

The invention relates to the field of cell biology, and in particular, to the study of circulating microvesicle structures that are produced by cells. The invention relates to compositions and methods for the isolation of microvesicles produced by cells, finding use in biomedical research and potential therapeutic applications.

BACKGROUND OF THE INVENTION

The term microvesicles (also known as microparticles) refers to a heterogeneous in vivo collection of membrane bound (i.e., encapsulated) biological structures. These structures are formed from lipid bilayer, which is the same lipid bilayer that comprises eukaryotic cell membranes. Microvesicles can reside within the cell, or in the extracellular environment. Microvesicle structures (intracellular and/or extracellular) are produced by nearly all mammalian cell types, as well as during in vitro cell culture.

The molecular composition of microvesicles is diverse, containing and/or transporting a variety of nucleic acids, proteins and lipids. Microvesicle molecular composition is generally reflective of the plasma membrane and antigenic content of the cell types, tissues and organs from which they originate. Mathivanan and Simpson, "Exosomes: extracellular organelles important in intercellular communication," *J. Proteomics* 73(10):1907-1920 (2010). Although protein composition of the microvesicles varies, most of these structures are enriched for various soluble protein markers, including HSP70, Hsc70, CD63, CD9, CD81 and others. Circulating microvesicles have also been reported to contain nucleic acids, including messenger RNAs, and relatively high levels of small RNAs and microRNAs.

Circulating microvesicles are associated with numerous cell functions, including intercellular (cell-to-cell) communication, removal of metabolic byproducts and toxins (including misfolded proteins, cytotoxic agents and metabolic waste), angiogenesis, tissue regeneration, endocytic recycling of the plasma membrane, selective removal of plasma membrane proteins and regulation of immune functions such as antigen presentation. Some microvesicles have been shown to transport messenger RNA (mRNA) and microRNA (miRNA), which is highly suggestive of microvesicles functioning as messengers that allow one cell type to regulate the activity of a distant cell type by acting as a shuttle that can merge with the distant cell and release its contents into that target recipient cell. This microvesicle shuttle can utilize the body fluids to travel to distant sites and control the activity of distant target cells.

Circulating microvesicles (cMVs), or synonymously, extracellular microvesicles (eMVs), describe an eclectic group of microvesicles that are released by cells, and therefore, exist in extracellular spaces and/or reside in body fluids. The mammalian body fluids that are known or suspected to contain cMVs include, but are not limited to, blood, urine, ascites fluid and cerebrospinal fluid. Secreted microvesicles are also found in cell culture media that has been exposed to cultured mammalian cells.

With regard to defining and categorizing the cMV molecules that can be found in body fluids, there is lack of consensus as to the nomenclature and description of the different types of cMV particles. Some literature distinguishes at least three subcategories of circulating microvesicles, based on their mechanistic origin. The molecular/cellular mechanisms that produce microvesicles are theorized to include (i) exocytosis of intracellular multivesicular bodies, (ii) outward budding, fission and shedding of plasma membrane, and (iii) byproducts of apoptosis. The diverse collection of circulating microvesicle structures can range in size from about 20 nanometers (nm) to upwards of about 1,000 nm (i.e., 1.0 micrometer, micron, or μm) in diameter.

The first recognized subgroup of cMVs are those produced by direct plasma membrane budding, fission and shedding. Some sources describe these shed microvesicles as generally large, namely with lower sizes limits of at least 100 nm or 200 nm, and with an upper size limit of about 1,000 nm in diameter. Some have proposed that these structures be termed "ectosomes" or "shedding microvesicles (SMVs)." Still other groups state that ectosome particles may be as small as 40 or 50 nm in diameter.

A second recognized subgroup of cMVs are exosomes, that is, the preformed microvesicles that are released from the cell following the exocytic fusion of intracellular multivesicular bodies with the plasma membrane. These exosome structures are generally smaller than ectosmoes, and have an upper size limit estimated to be about 100, 150 or 200 nm, and a lower size limit of about 40 nm or 50 nm. However, various sources differ in their size-based definitions for exosomes, and this size distinction remains unresolved.

A third group of structures is the apoptotic blebs released by dying cells. These membrane structures have a less well defined size range, and may be anywhere from about 50 nm to about 5,000 nm in diameter.

A unified microvesicle nomenclature and classification system utilizing broadly accepted definitions has been elusive in the field. In the literature, microvesicles have been alternatively referred to as microparticles, nanoparticles, exosomes, ectosomes, epididimosomes, argosomes, exosome-like vesicles, promininosomes, prostasomes, dexosomes, texosomes, archeosomes, oncosomes, exosome-like vesicles, apoptotic blebs, and shedding microvesicles. In some publications, uses of these terms is conflicting or overlapping. Simpson and Mathivanan (2012), "Extracellular Microvesicles: The Need for Internationally Recognized Nomenclature and Stringent Purification Criteria". *J Proteomics Bioinform* (2). doi:10.4172/jpb.10000e10. One source suggests that a preferred nomenclature for circulating microvesicle is based on the microvesicle's mechanism of origin. Namely, these categories would be (i) the ectosomes produced by membrane budding, (ii) the exosomes produced by the exocytosis to intracellular multivesicular bodies, and (iii) the membrane blebs produced by the process of apoptosis.

The function of extracellular microvesicles is not clearly understood, although they are theorized to act as nanoshuttles for the transport and delivery of information from one location and/or cell type to distant locations and/or other cell types. Exosomes are theorized to be involved in a wide variety of physiological processes, including cardiac disease, adaptive immune responses to pathogens, and in tumor biology. It is suggested that microvesicles may play roles in tumor immune suppression, metastasis, and tumor-stroma interactions. Microvesicles are thought to play a role in immune system cellular communication, for example, involving dendritic cells and B cells.

The ubiquitous presence of circulating microvesicles in body fluids, their association with a broad range of physiological processes, as well as their elevated levels in human disease, suggest that microvesicles can potentially serve as tools in molecular medicine as measures of physiological state, disease diagnostics, and possibly therapeutic targeting.

Although the study of microvesicles/exosomes had been greatly advanced with the development of analytical systems such as nanoparticle tracking analysis (NTA) and fluorescent nanoparticle tracking analysis (FNTA), other technical challenges remain.

One of the significant technical challenges in current research in microvesicles is the problem of how to efficiently isolate the microvesicles from various sources. Current methodologies to isolate secreted microvesicles, including but not limited to exosomes, are constrained by technical limitations and other drawbacks. These known methodologies are labor intensive, time-consuming and costly. See (i) Van der Pol et al., "Optical and non-optical methods for detection and characterization of microparticles and exosomes," Journal of Thrombosis and Haemostasis (2010), doi: 10.1111/j.1538-7836.2010.04074.x; (ii) Dragovic et al., "Sizing and phenotyping of cellular vesicles using Nanoparticle Tracking Analysis," Nanomedicine: Nanotechnology, Biology and Medicine (2011), doi:10.1016/j.nano.2011.04.003; and (iii) Tauro et al., "Comparison of ultracentrifugation, density gradient separation, and immunoaffinity capture methods for isolating human colon cancer cell line LIM1863-derived exosomes," *Methods* 56(2):293-304 (print February 2012, Epub Jan. 21, 2012), doi: 10.1016/j.ymeth.2012.01.002.

Historically, ultracentrifugation is the traditional method for microvesicle isolation. Generally, centrifugation is the process whereby a centrifugal force is applied to a mixture, whereby more-dense components of the mixture migrate away from the axis of the centrifuge relative to other less-dense components in the mixture. The force that is applied to the mixture is a function of the speed of the centrifuge rotor, and the radius of the spin. In most applications, the force of the spin will result in a precipitate (a pellet) to gather at the bottom of the centrifuge tube, where the remaining solution is properly called a "supernate" or "supernatant." In other similar applications, a density-based separation or "gradient centrifugation" technique is used to isolate a particular species from a mixture that contains components that are both more dense and less dense than the desired component (e.g., OptiPrep™).

During the circular motion of a centrifuge rotor, the force that is applied is the product of the radius and the angular velocity of the spin, where the force is traditionally expressed as an acceleration relative to "g," the standard acceleration due to gravity at the Earth's surface. The centrifugal force that is applied is termed the "relative centrifugal force" (RCF), and is expressed in multiples of "g" (or "×g").

The centrifugation procedures that have been used to isolate circulating microvesicles can incorporate as many as five centrifugation steps, with at least two of these spins requiring centrifugal forces in excess of 100,000×g for several hours. Generally, ultracentrifugation is centrifugation conditions that produce forces in excess of 100,000×g. These ultracentrifugation procedures are time consuming and labor intensive, and furthermore, are constrained by the requirement for expensive ultracentrifugation equipment.

Size exclusion chromatography can also be used to isolate microvesicles, for example, by using a Sephadex™ G200 column matrix. This approach is also time consuming and the yields are inconsistent.

Selective immunoaffinity capture (including immuno-precipitation) can also be used to isolate circulating microvesicles, for example, by using antibodies directed against the epithelial cell adhesion molecule, a type-I transmembrane cell-surface protein (also known as EpCAM, CD326, KSA, TROP1). The anti-EpCAM antibodies can be coupled to magnetic microbeads, such as Dynabeads® magnetic beads. This method has very low yields compared to other methods, and is costly due to the use of the immuno-reagents and magnetic beads, and further, these system reagents cannot be reused for subsequent isolations.

The in vitro culture of mammalian cells is a critical tool in the study of cell biology, including microvesicle function. Historically, mammalian cells (including both adherent and non-adherent lines) are cultured using a defined minimal media supplemented with a blood serum or blood plasma. There exists a wide variety of minimal growth media, which a user would select to optimize the growth of the particular cell line of interest. Examples of classic defined media include Basal Medium Eagle (BME), Dulbecco's Modified Eagle's medium (DMEM), minimal essential medium (MEM), F10 Nutrient Mixture, Ham's tissue culture medium, Ham's F12 medium and RPMI-1640 medium. Countless variations of minimal defined media have been developed since the original formulations were developed. In addition, individual laboratories will often develop their own unique formulations in order to optimize their particular experimental system.

These minimal media contain various concentrations of defined components, including, for example, but not limited to, the 20 amino acids, purine and pyrimidine nucleotides and/or nucleotide precursors, phospholipids and phospholipid precursors, vitamins (as parts of coenzymes), lipoic acid, a carbon source such as glucose, and inorganic ions. Some formulations add additional components, such as growth factors and hormones, and/or vary the concentrations of the various components.

Complete growth medium for most in vitro cultured mammalian cells requires supplementation of the minimal defined media with a blood serum or blood plasma, most typically heat inactivated blood sera. This supplementation is typically on the order of 1% to 20% blood serum by volume of the minimal defined media.

The serum that is used to supplement the minimal defined medium can be from a variety of sources, for example, bovine, equine (horse), human, mouse, rat and goat. Bovine serum is most commonly used in laboratory settings. Serum supplements that are derived from age-staged animals can also be used, and may be desirable for their various growth properties. For example, bovine serum can be age-staged as fetal bovine serum (FBS), calf serum (CS), newborn calf serum, or adult bovine serum. Heat inactivated FBS is frequently used in many applications. Heat inactivated FBS is frequently used in combination with DMEM to form a complete growth media for many types of mammalian cells.

It is known that FBS contains an abundance of endogenous bovine microvesicles, including exosomes. These endogenous microvesicles can exert effects on cultured cells when the FBS is used as a supplement to make a complete culture medium. Sakwe et al., "Fetuin-A (alpha-2HS-Glycoprotein) Is a Major Serum Adhesive Protein That Mediates Growth Signaling in Breast Tumor Cells," *J Biol. Chem.* 285(53): 41827-41835 (2010). These endogenous microvesicles may impact the growth or differentiation of cells maintained in culture, and may skew or interfere with experimental results and experimental interpretation. In other examples, the endogenous microvesicles found in blood serum can copurify with microvesicles that are produced by the cultured cell lines of interest. Bhatnagar et al., "Exosomes released from macrophages infected with intracellular pathogens stimulate a proinflammatory response in vitro and in vivo," *Blood* Vol. 110, no. 9:3234-3244 (2007).

Although some cultured cell lines can be grown for a short time in minimal media in the absence of a serum supplement, this is not always possible. For these reasons, it would be desirable to remove or deplete cell culture media of any endogenous microvesicles that are introduced through the traditional addition of blood serum or blood plasma components in cell culture media.

What is needed in the art are methods for the rapid and inexpensive isolation of microvesicles, specifically circulating microvesicles, for example, exosomes and microsomes. Preferably, these methods will utilize common laboratory reagents and apparatus, and will not require high speed centrifugation, such as ultracentrifugation. What is needed in the art are methods for the isolation of circulating microvesicles, where the methods utilize low speed centrifugation that uses centrifugal forces significantly less than 100,000×g.

Furthermore, what is also needed in the art are methods for generating cell culture media that are free of endogenous microvesicles, or have reduced concentrations of endogenous microvesicles compared to traditional complete media. What is needed in the art are methods for generating blood serum or blood plasma media supplements that are free of endogenous microvesicles, or have reduced concentrations of endogenous microvesicles compared to untreated blood serum or plasma.

SUMMARY OF THE INVENTION

The present invention provides methods for the rapid and inexpensive isolation of microvesicles, specifically circulating microvesicles such as exosomes. These methods utilize common laboratory reagents and apparatus, and do not require high speed centrifugation, such as ultracentrifugation. These methods of the invention also do not require the use of gradient sedimentation for the isolation of circulating microvesicles.

These methods can be used to isolate microvesicles from any source, including biofluids, such as but not limited to, blood serum, blood plasma, ascites fluid, urine, or cerebrospinal fluid (CSF). These methods can also be used to isolate microvesicles from cell culture media that has been used to culture mammalian cells in vitro.

The microvesicles isolated by the methods of the invention, e.g., the exosomes, have the characteristics of true microvesicles, as assayed by protein markers, small RNAs and microscopic examination of size and structure of the microvesicles.

In some embodiments, the invention provides methods for isolating secreted microvesicles from a liquid sample, where those methods comprise (i) combining the liquid sample with a precipitation solution that minimally contains polyethylene glycol (PEG) having an average molecular weight of about 8,000 Daltons, (ii) incubating the mixture; typically at 4° C., and typically overnight, (iii) centrifuging the mixture to form a pellet and a supernatant, most advantageously, in a low speed centrifugation, (iv) removing the supernatant after the spin, and (v) recovering the pellet by resuspending in a resuspension solution. In some aspects of these methods, the secreted microvesicles that are isolated are exosomes. In some aspects, isolation of exosomes is confirmed by determining whether or not the isolated material is enriched for protein or nucleic acid makers that are known to preferentially segregate with exosomes. Confirmation can also be obtained by physical analysis where microvesicles having an average diameter between about 40 nm and about 150 nm is consistent with exosome isolation.

The nature of the samples from which the microvesicles are isolated can be diverse. In some embodiments, the liquid sample is a conditioned cell culture media, i.e., a culture media that has been used to culture cells. The liquid sample can also be any type of biofluid, for example but not limited to whole blood, blood serum, blood plasma, urine, saliva, sputum, breast milk, ascites fluid, synovial fluid, amniotic fluid, semen, cerebrospinal fluid, follicular fluid and tears.

The precipitation solution is typically prepared as a 50% by weight solution of PEG, e.g., PEG-8,000, although other concentrations ranging from 30%-50% can also be used. That is to say, the precipitation solution has a concentration of PEG that is between about 300 mg/mL and 500 mg/mL. The liquid sample and the precipitation solution are most typically combined in a volume ratio of about 5:1 (five parts liquid sample, one part precipitation solution), although other volume ratios can be used as well, for example, in the range from 1:1 to 10:1.

Using these methods, the centrifuging step the generate the microvesicle pellet can advantageously be done in a low-speed centrifuge, in contrast to other methods for isolating microvesicles which require a high speed centrifugation, such as ultracentrifugation. For example, using the presently disclosed methods, centrifugal forces of about 1,500×g are sufficient. This degree of force is a function of both speed of the spin and the radius of the spin. One of skill in the art will know how to determine if a particular rotor and speed combination produces sufficient centrifugal force to use in the present methods.

In these methods, resuspending the pellet after the centrifugation step will most often entail resuspending in a volume of resuspension solution that is less than the starting volume of the liquid sample.

In other aspects, the invention also provides method for producing serum that is depleted or partially depleted of endogenous microvesicles, or the microvesicles are below the limits of detection. These methods comprise (i) combining the serum with a precipitation solution that minimally contains polyethylene glycol (PEG) having an average molecular weight of about either 8,000 or 10,000 Daltons, (ii) incubating the mixture, typically at 4° C., and typically overnight, (iii) centrifuging the admixture to form a pellet and a supernatant, most advantageously, in a low speed centrifugation, (iv) recovering the supernatant after the spin, and (v) transferring the supernatant to a suitable container, where the supernatant is the exosome-depleted serum. This supernatant then finds use as a supplement for complete cell growth media.

In some aspects, the precipitation solution to produce exosome-free or exosome-depleted serum is prepared as a 50% by weight solution of PEG, although other concentrations ranging from 30%-50% can also be used. That is to say, the precipitation solution has a concentration of PEG that is between about 300 mg/mL and 500 mg/mL. The serum and the precipitation solution are most typically combined in a volume ratio of about 5:1 (five parts serum, one part precipitation solution), although other volume ratios can be used as well, for example, in the range from 1:1 to 10:1.

In some aspects, the microvesicle-depleted serum comprises microvesicles in a concentration of not more than about $10^4$ microvesicles per milliliter (mL). The serum that is used to prepare the exosome-depleted serum is not limited. For example, the starting serum that is used to produce the exosome-depleted serum can be any serum including but not limited to bovine serum, horse serum, human serum, rat serum, mouse serum, rabbit serum, sheep serum, goat serum, lamb serum, chicken serum and porcine serum. The serum can be fetal bovine serum.

BRIEF DESCRIPTION OF THE DRAWINGS

FIG. 16A shows the testing for these RNA sequences in standard (untreated) FBS, and FIG. 16B shows the testing for these RNA sequences in exosome-depleted FBS (Exo-FBS).

DETAILED DESCRIPTION OF THE INVENTION

Figure 1:
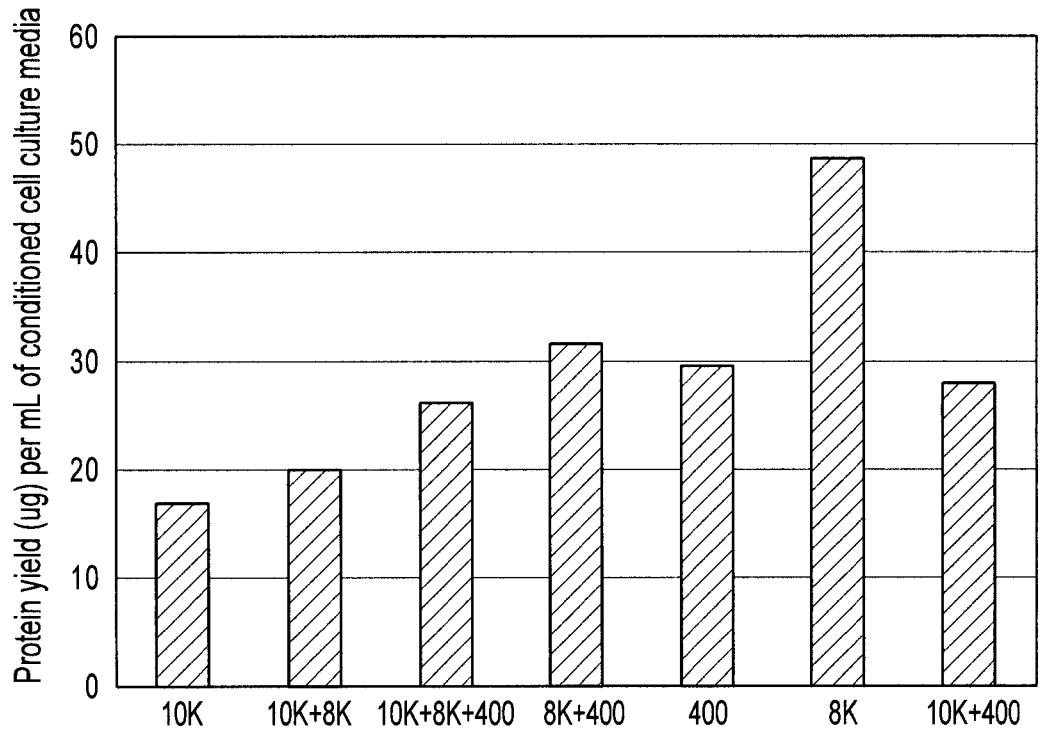
FIG. 1 provides a histogram summarizing the results of an experiment that analyzes the ability of different PEG polymers and PEG polymer combinations to isolate total protein from conditioned cell culture media.

The present invention provides compositions and methods for producing preparations of isolated secreted microvesicles from a liquid sample. The invention also provides methods for producing blood serum that has been at least partially depleted of microvesicles. These methods have a number of advantages over the state of the art, which will be apparent from the discussion herein.

I. Definitions

As used in this application, the terms "cells" or "cell culture" or "cell lines" or "cell culture media" refers to eukaryotic cells, and more specifically (but not exclusively), to higher eukaryotic cells such as mammalian cells, as in human cells or mouse cells. The description of the present invention does not pertain to prokaryotic cells such as eubacteria cells or *Archaea* cells.

As used herein, the term "microvesicle" refers generally to any plasma membrane bound particle, that may reside within the cell, or in the extracellular environment. These structures are not limited in any way with regard to in vivo localization (e.g., intracellular or extracellular), in a body fluid, in a cell culture media, generated by in vitro cultured cells, mechanism of origin or size characteristics. In some embodiments, a microvesicle can range in size with a lower size limit of at least about 20 nanometers (nm) in diameter, or alternatively, 30 nm, or 40 nm, or 50 nm in diameter. In some embodiments, a microvesicle has an upper size limit of not more than about 1,000 nm (i.e., 1.0 micrometer, micron, or μm), or alternatively, not more than about 1,500 nm, about 2,000 nm or about 2,500 nm.

As used herein, the term "secreted microvesicle" is used synonymously with "circulating microvesicle (cMV)" or "extracellular microvesicle (eMV)," and refers to a subset of microvesicles that are found in an extracellular space under normal physiological conditions. As used herein, it is not intended that the term "circulating microvesicles" to be limited to microvesicles of any particular size or size range, or any particular production mechanism. For example, but not limited to, a cMV of the invention can be produced by (i) exocytosis from multivesicular bodies to produce exosomes, (ii) budding, fission and shedding of microvesicles directly from a cytoplasmic membrane, and (iii) membranous blebs caused by programmed cell death leading to the formation of apoptotic bodies. As used herein, the term "cMV" is not limited to microvesicles of any particular size or size range.

Although mechanistic theories for the endogenous production of circulating microvesicles are found in the scientific literature, any knowledge of such mechanisms is not required to make or used the present invention. It is not intended that the term "circulating microvesicles" as used herein be limited in any way with regard to the mechanism of their in vivo production.

As used herein, the term "shedding microvesicle (SMV)" refers to a class of microvesicles that are produced by cells using a mechanism of direct plasma membrane budding, fission and shedding to produce microvesicles that are released by a cell into an extracellular environment. As used herein, it is not intended that an SMV of the invention be limited by any particular size or size range.

As used herein, the term "exosome" refers to a subset of circulating microvesicles that are preformed microvesicles that are released from the cell following the exocytic fusion of intracellular multivesicular bodies with the plasma membrane, i.e., exosomes have an endocytic origin. As used herein, it is not intended that an exosome of the invention be limited by any particular size or size range.

As used herein, the term "apoptotic body" refers to a subset of circulating microvesicles that are produced as a result of apoptotic cell destruction. As used herein, it is not intended that an apoptotic body of the invention be limited by any particular size or size range.

As used herein, the term "isolating," or "to isolate," refers to any artificial (i.e., not naturally occurring) process for treating a starting material, where the process results in a more useful form of a molecule or structure of interest that is in the starting material. The "more useful form" of the molecule or structure of interest can be characterized in a variety of ways, no one of which is limiting. For example, as used herein, the invention provides methods for isolating secreted microvesicles from conditioned cell culture media. Further, for example, the process for isolating can result in:
(i) the molecule of interest having a greater concentration in the isolated form compared to the starting material (e.g., concentrating),
(ii) the removal of any amount or any type of impurities from the starting material (e.g., purifying),
(iii) an increase in the ratio of the amount of molecule of interest to the amount of any undesired component in the starting material (e.g., enriching),
(iv) any artificial process for removing a molecule or structure of interest from its natural source or location;
(v) any artificial process for separating a molecule or structure of interest from at least one other component with which it is normally associated (e.g., purifying), or
(vi) any combination of (i), (ii), (iii), (iv) or (v).

Similarly, as used herein, the term "isolated" generally refers to the state of the molecule or structure of interest after the starting material has been subjected to a method for isolating the molecule of interest. That is to say, isolating a molecule of interest from a starting material will produce an isolated molecule. For example, the methods of the invention are used to produce preparations of isolated microvesicles. These preparations of microvesicles have been isolated from their natural source, for example, from urine, or from conditioned cell culture media.

As used herein, the term "purifying" or "to purify" a molecule or structure of interest refers to a process for removing at least one impurity or contaminant from a starting material. For example, purifying a molecule of interest from a starting material refers to a process for removing at least one impurity from the starting material to produce a relatively more pure form of the molecule of interest.

As used herein, the term "substantially purified" refers to molecules or structures of interest that are removed from their natural environment or from a starting material (i.e., they are isolated) and where they are largely free from other components with which they are naturally associated or substantially free of other components that may render future use or study sub-optimal, difficult or impossible.

As used herein, the terms "purified" or "partially purified" refers to molecules or structures of interest that are removed from either (1) their natural environment, or from (2) a starting material (i.e., they are isolated), and where (a) at least one impurity from the starting material has been removed, or (b) at least one component with which the molecule is naturally associated has been removed. A "purified" or "partially purified" molecule may still contain additional components that may render future use or study of the molecule sub-optimal, difficult or impossible.

As used herein, the term "enriching" (and "enriched" and the like) refers to a process whereby a molecule of interest that is in a mixture has an increased ratio of the amount of that molecule to the amount of other undesired components in that mixture after the enriching process as compared to before the enriching process.

As used herein, the term "concentrating" refers to a process whereby a molecule of interest that is in a mixture that has been subjected to that process has a greater concentration after the process as compared to the concentration of the molecule in the mixture before the process.

As used herein, the term "depleted" refers to a mixture containing an undesirable component, where that undesirable component has been (i) completely removed from the mixture, (ii) sufficiently removed from the mixture to be undetectable, or (iii) partially removed from the mixture such that its concentration in the mixture is significantly reduced. For example, a blood serum that has been depleted of endogenous microvesicles may contain no microvesicles, or may contain no detectable microvesicles, or may contain a reduced level of microvesicles compared to the untreated serum.

As used herein, the expression "cell culture media" refers to any growth media that can support in vitro cell growth of a designated cell line. Such media can be supplemented or non-supplemented, for example, with 10% by volume, heat-inactivated fetal calf serum.

As used herein, the expression "minimal defined cell culture media" or "minimal media" refers to any culture media where each component is defined by name and the concentration of each component is known. Minimal defined cell culture media generally does not contain a serum supplement. For example, Dulbecco's Modified Eagle's medium (DMEM) is a defined minimal cell culture media. Minimal defined cell culture media generally can be used to culture cells in vitro, but not for extended periods of time.

As used herein, the expression "complete cell culture media" refers to a culture media that comprises a defined minimal cell culture media, and in addition, also comprises a complex supplement that enhances the growth properties of the culture media. For example, a blood serum supplement is commonly added to a minimal media to produce a complete cell culture media. Fetal calf serum (FBS or FCS) is a common supplement (10% by volume) that is added to a minimal media to produce a complete culture media. Complete culture media are used to culture cells in vitro for indefinite (long) periods of time.

As used herein, the expression "conditioned cell culture media" refers to any cell culture media (including complete media or minimal media) that has been exposed to live cells in culture. Conditioned cell culture media comprises not only the defined components of the minimal media and the serum supplement, but also contains additional components that the living cultured cells have produced. In many cases, conditioned cell culture media is a serum-free media.

II. Methods for Isolating Secreted Microvesicles

The present invention provides methods for the isolation of secreted microvesicles from liquid samples. Generally, the methods for isolating comprise the following steps.

A) Preparing a Precipitation Solution

In some embodiments, the precipitation solution that is used is an aqueous solution comprising at least one polyethylene glycol (PEG) species that has a molecular weight of between 400 Daltons to 8,000 Daltons. In one preferred embodiment, the PEG that is used is PEG-8,000. In other embodiments, the precipitation solution comprises PEG-10,000. The nature of the solution that is used to make the PEG precipitation solution is not particularly limited, and can be, for example, water, or any physiological saline, such as phosphate buffered saline.

A precipitation solution is prepared by dissolving the PEG species (e.g., PEG-8,000) in an aqueous phase. This precipitation solution can contain, for example, between 300 milligrams per milliliter (mg/mL) to about 500 mg/mL of the PEG polymer (i.e., 30%-50% PEG by weight). A concentration of about 500 mg/mL of PEG in the precipitation solution was preferred in some embodiments.

The PEG is dissolved in any suitable aqueous solution, including simply water. It is not intended that the aqueous solution used to prepare the PEG precipitation solution be limited in any way.

In some embodiments, the PEG precipitation solution is typically prepared in a standard phosphate buffered saline (PBS) solution, although the PBS is not strictly required. PBS is isotonic and physiologically compatible, and maintains pH and osmolality near physiological levels. It is widely used when handling cell cultures and complex biomolecules. A variety of formulations of PBS are known in the literature, any of which can find use with the invention.

In one embodiment, the PBS uses the following formulation, which is one common formulation for PBS.

| PBS Formulation Component | | Concentration millimol/L (mM) |
|---|---|---|
| sodium chloride | NaCl | 137 |
| potassium chloride | KCl | 2.7 |
| disodium hydrogen phosphate, (dibasic) | $Na_2HPO_4$ | 10 |
| potassium dihydrogen phosphate, (monobasic) | $KH_2PO_4$ | 2.0 |
| pH to 7.4 | | |

B) Combining the Precipitation Solution with the Liquid Sample

To initiate the precipitation of the exosomes, the precipitation solution is added to the liquid sample (e.g., conditioned cell culture media), generally in a volume ratio of about one part of PEG precipitation solution to about 5 parts of liquid sample (1:5). It is not intended that the invention be limited to this ratio or quantity of PEG used to precipitate the exosomes. Depending on the liquid sample, other volume ratios may be useful, for example, any ratio (precipitation solution to liquid sample) between about 1:1 to about 1:10. After combining the precipitation solution and the liquid sample, the tube or vessel with these two components is mixed or agitated to fully disperse the components. In some embodiments, gentle mixing, such as by swirling or inverting, is preferred.

C) Incubating the Resulting Mixture

The resulting mixture is then incubated. The incubation can be with any degree of cooling, for example at 5° C., although such cooling is not required. The incubation times can vary, and are not in any way limiting. For example, incubation can be anywhere between 30 minutes to overnight (e.g., 16 hours). The incubation can be with or without mixing, and the mixing during the incubation period can be constant or intermittent.

D) Centrifuging the Mixture

Following the incubation, the mixture is subjected to a centrifugation. The centrifugation typically forms a pellet and a supernatant, although pelleted material may not be visible to the eye. In contrast to the prior art, this centrifugation does not require ultracentrifugation, e.g., does not require centrifugal forces in excess of 100,000×g. This centrifugation can be done at slower speeds, for example, to generate RCF values of not more than 30,000×g, or not more than 20,000×g, or not more than 12,000×g, or not more than 10,000×g, or not more than 5,000×g, or not more than 2,000×g, or not more than 1,500×g. In one embodiment, a centrifugation producing 1,500×g is preferred. The length of time for centrifugation is not limiting. In some embodiments, the centrifugation is for 30 minutes.

E) Removing the Supernatant

Following the spin, the resulting supernatant is carefully removed so not to disturb the pellet, and this supernatant is discarded.

F) Resuspending the Pelleted Material

After removal of the supernatant, the pellet is resuspended in any desired resuspension solution and collected for further analysis. The resuspension solution can use either water, phosphate buffered saline (PBS), or any other suitable aqueous, such as any isotonic solution. The volume used for the resuspension is most typically the smallest possible practical volume, and is typically many times smaller than the volume of the original liquid sample comprising the secreted microvesicles. In some embodiments, the volume of the resuspension solution is smaller by at least one order of magnitude than the volume of the original liquid sample.

After the centrifugation step, it is possible that a pellet may not be visible to the eye. Although there may not be a visible pellet, there still may well be centrifuged material at the bottom of the centrifuge. In this case, carefully remove the supernatant, being careful not to disturb the bottom area of the centrifuged vessel. After removing the supernatant, add a reasonably small volume of resuspension liquid to the tube, and agitate to collect any centrifuged material, e.g., microvesicles.

F) Other Optional Steps

These methods generate preparations of isolated microvesicles, where the preparations can comprise substantially purified or partially purified microvesicles, preparations enriched in microvesicles, and/or preparations comprising microvesicles that have been concentrated.

Optionally, the methods for isolating microvesicles can include additional step or steps prior to admixing the liquid sample with the precipitation solution. For example, the liquid sample can be subjected to an optional centrifugation or filtration step for the purpose of removing unwanted whole cells, cellular debris or other precipitates from the sample prior to mixing with the PEG precipitation solution.

The methods of the invention can be adapted to isolate intracellular membrane-bound structures (e.g., organelles or endosomes) from a preparation of cells following disruption of the cellular membrane. This can be accomplished by methods for cell membrane disruption that preserve the integrity of smaller intracellular membrane bound organelles, for example, by mechanical disruption such as shearing.

In some aspects, the methods of the invention are optimized for the isolation of microvesicles from conditioned cell culture media, where the cell culture media can contain a serum supplement, or be serum-free. In other aspects, the methods for microvesicles isolation can be optimized for various biofluids. For example, isolation of microvesicles from urine or conditioned cell culture media is optimized by the use of a precipitation solution comprising PEG-8,000. Also for example, the isolation of microvesicles from blood serum or other body fluids is optimized by the use of a precipitation solution comprising PEG-10,000.

III. Liquid Samples

The present invention provides methods for isolating circulating microvesicles from liquid samples. It is not intended that the nature of the liquid samples be in any way limited, and can be any liquid sample that contains microvesicles. Advantageously, very small volumes of liquid sample can be used, for example, as little as 1.0 mL, or 2.0 mL. or 3.0 mL. or 5.0 mL of starting sample can be used.

In some embodiments, the liquid sample can be conditioned cell culture media that has been used to culture a cell line in vitro that has produced microvesicles, and therefore, those microvesicles are now contained in the conditioned media. The conditioned cell culture media can be a complete media (containing a serum supplement), or a serum-free culture media.

In some embodiments where the conditioned cell culture media is a complete media comprising a serum supplement, the serum supplement that is used can be a serum that has been depleted of any endogenous circulating microvesicles prior to addition of the supplement to the defined minimal growth media. The present invention also provides methods for producing such exosome-depleted serum.

In some embodiments, the liquid sample is a biofluid (synonymous with body fluid). The body fluid that is used in the analysis is not particularly limited. Microvesicles can be isolated from any body fluid using the methods of the invention, even though a particular body fluid is not itemized herein, as it is intended that the present methods find use with any and all body fluids. For example, body fluids that can be analyzed by the methods of the invention include, but are not limited to, amniotic fluid, blood serum, blood plasma, breast milk, cerebrospinal fluid, lymph, mucus (including nasal drainage and phlegm), pericardial fluid, peritoneal fluid, semen, synovial fluid, tears, urine and ascites fluid.

IV. Precipitation Reagents

The present invention provides methods for the isolation of microvesicles from liquid samples, where the methods utilize a precipitation solution, combined with the liquid sample, to initiate the microvesicle (or exosome) precipitation and isolation. The precipitation solution that is used is an aqueous solution comprising at least one polyethylene glycol (PEG) species that has an average molecular weight between and including 400 Daltons and 8,000 Daltons. In one preferred embodiment, the PEG that is used is PEG-8,000. In other embodiments, the precipitation solution comprises PEG-10,000.

The nature of the aqueous phase that is used to make the PEG precipitation solution is not particularly limited, and can be, for example, only water, or a physiological saline, such as phosphate buffered saline. When PBS is used to make the precipitation solution containing the PEG-8,000, the resulting solution is termed ExoQuick-TC™ manufactured by System Biosciences, Inc. (SBI; Mountain View, Calif.). Combinations of PEG polymer species can also be used in the methods of the invention.

The PEG polymer that is used is not limited to any particular purity, and the choice of purity is dependent on the users' requirements. Regardless of the purity that is used, it remains a feature of the invention that the average molecular weight is defined, for example, as a PEG polymer with an average molecular weight (i.e., Daltons) of 8,000 Daltons, or alternatively, 10,000 Daltons. PEG polymers are available from a variety of commercial manufacturers, any of which find use with the invention.

The concentration of the PEG polymer in the precipitation solution is not particularly limited. As a guide, 300-500 mg/mL of the PEG species can be used as a guide, but users can define their own optimal conditions that may lie outside this range. Concentrations that lie outside this range are also within the scope of the invention. In some embodiments, PEG polymer is in a concentration of about 500 mg/mL in the precipitation solution. These weight concentrations can also be expressed as molar concentration equivalents, e.g., about 0.06 to 1.25 mol/L.

Various volumes (volume ratios) of the precipitation solutions can also be used when being combined with the liquid sample. In some embodiments, the volume of liquid sample is typically equal to or in excess of the volume of the added precipitation solution. As a guide, a ratio of precipitation solution to liquid sample ranging from 1:1 to about 1:10 can be used. A ratio of about 1:5 is typical. However, this feature is not limiting, and volume ratios that lie outside this range are also within the scope of the invention.

V. Methods for Producing Microvesicle-Depleted Blood Serum and Blood Plasma

The invention provides methods for removing microvesicle structures from a blood plasma or a blood serum, thereby creating a microvesicle (or exosome)-depleted plasma or serum. This method entails adding a precipitation solution to the plasma or serum, incubating the admixture, subjecting that mixture to a low speed centrifugation, and then isolating and preserving the supernatant. This supernatant is now depleted of microvesicle structures, where the supernatant has no detectable microvesicle structures, or where the supernatant comprises significantly reduced levels of microvesicle structures.

The precipitation solution comprises one or a combination of PEG polymers. For example, the precipitation solution can comprise a PEG polymer of 8,000 Daltons, or about 10,000 Daltons, for example. Precipitation conditions similar to the conditions to producing isolated microvesicles are utilized.

It s not intended that the invention be limited to the generation of any one type of microvesicle-depleted plasma or serum. For example, a wide variety of plasma and serum are used for research purposes, and all of these plasma and sera have advantageous sues when they have been depleted of microvesicle structures.

For example, the plasma or serum that can be produced as a microvesicle-depleted product includes, but is not limited to, bovine serum, horse serum, human serum, rat serum, mouse serum, rabbit serum, sheep serum, goat serum, lamb serum, chicken serum and porcine serum. Such sera and plasma can also be age staged, for example, fetal bovine serum, calf bovine serum, newborn calf bovine serum or adult bovine serum.

PEG-10,000 (e.g., 50% by weight in PBS) can be used in a precipitation solution to deplete fetal bovine serum (FBS) of endogenous exosomes, thereby generating an exosome-depleted FBS suitable for use in cell culture. This product is termed Exo-FBS™ manufactured by System Biosciences, Inc. (Mountain View, Calif.). Exo-FBS™ is devoid of bovine CD63 positive exosomes and does not have any measurable bovine microRNAs. Exo-FBS™ supports cell growth equivalent to untreated FBS, and in many types of cells in culture.

EXAMPLES

The following examples are offered to illustrate, but not limit, the claimed invention. It is understood that various modifications of minor nature or substitutions with substantially similar reagents or components will be recognizable to persons skilled in the art, and these modifications or substitutions are intended to be included within the spirit and purview of this application and within the scope of the appended claims.

Example 1

Development of Novel Systems for Isolation of Circulating Microvesicles

In an effort to develop new and improved methods for the isolation of circulating microvesicles, including exosomes, experiments were undertaken to test new approaches to microvesicle isolation.

Exosomes have been reported to have diameters ranging anywhere from about 40-200 nm. Lentivirus particles have an average diameter of about 80 nm, a size that is within the estimated range of exosome size. Formulations of polyethylene glycol (PEG-6000) had been previously used to precipitate and concentrate lentiviral particles from conditioned cell culture medium (Lewis and Metcalf, *Applied and Environmental Microbiology*, Vol. 54, No. 8 (1988). Because exosomes have similar diameters to a lentiviral particle, it was hypothesized that PEG formulations might be used to isolate exosomes from conditioned cell culture media that had been used to culture exosome-producing cell lines in vitro, and additionally, may also be used to isolate exosomes from other liquids such as biofluids.

Any PEG polymer species defined by a particular molecular weight (e.g., PEG-8,000 or PEG-10,000) is in fact a mixed population of PEG molecules of varying lengths, but where the molecule population is characterized by its average molecular weight. It is understood that when a reagent such as PEG-8,000 is specified, the vast preponderance of molecules in that preparation will have a molecular weight of about 8,000 daltons (within the accuracy range of experimental determination), but the population of molecules will also contain some small fraction of molecules that are slightly smaller and slightly larger than 8,000 daltons.

A matrix of varying PEG polymer sizes was used to test whether exosomes could be recovered from culture medium that has been conditioned using exosome-producing cells in serum-free conditions. Conditioned media was obtained from the culture of human embryonic kidney (HEK)-293 cells in 10 mL media in serum-free conditions. Fresh serum-free media was applied to an established HEK-293 cell culture, incubated for 2 days, and then collected. The conditioned media samples were then centrifuged at 1500×g for 30 minutes to remove whole cells or cell debris.

In these protocols, the following reagent sources are noted.

| Polyethylene Glycol species | Description | Source | Catalog Number |
|---|---|---|---|
| PEG-400 | Liquid, 500 mL | USB Products Corp. (now Affymetrix, Inc., Santa Clara, CA) | 19957 |
| PEG-8,000 | Flakes, 5 kg | USB Products Corp. (now Affymetrix, Inc., Santa Clara, CA) | 19959 |
| PEG-10,000 | Flakes, 2 kg | Sigma-Aldrich Co. (St. Louis, MO) | P6667 |

A precipitation solution was prepared that contained the various PEG species (e.g., the PEG-8,000 ExoQuick-TC™ reagent). In the case where PEG-8,000 was used, that PEG was tested using a broad range of molar concentrations from about 0.06 mol/L to 1.25 mol/L. From this range, optimal conditions were identified using between about 300 milligrams per milliliter (mg/mL) to about 500 mg/mL of the PEG polymer. The PEG in the precipitation solution was most frequently in a concentration of about 500 mg/mL. The PEG precipitation was typically prepared in a standard phosphate buffered saline (PBS) solution. This PEG stock solution was a clear, slightly viscous liquid that was stored at 5° C.

To initiate the precipitation of the exosomes, the precipitation solution was added to the conditioned cell media at a ratio of about one part PEG solution to about 5 parts media sample (1:5). A range of ratios was tried, from 1:1 to about 1:10. All were effective to some degree as measured by total protein measurements. The admixture was mixed by inversion.

The resulting mixture was incubated at 5° C. for times that varied between 30 minutes to overnight, most typically 12-16 hours. Following the incubation, the mixture was centrifuged (1,500×g) for 30 minutes.

Following the spin, the resulting supernatant was removed and discarded, and the pellet was resuspended and collected for further analysis. The resuspension used was either water or phosphate buffered saline (PBS). The volume used for the resuspension was most typically smaller by at least one order of magnitude than the volume of the original media sample.

It was first demonstrated that protein could be isolated using the various PEG reagents. This result was consistent with exosome recovery. See FIG. 1. Subsequently, Western blot analysis was used to demonstrate that the recovered proteins included proteins that are known to be abundant in microvesicles.

Additionally, NANOSIGHT® (NanoSight Ltd, Wiltshire, UK) instrumentation for nanoparticle tracking analysis (NTA) was also used to count, size and visualize the particles that were being isolated using the various PEG formulations. Cumulatively, these observations confirmed that the materials being preferentially isolated using the PEG protocols were consistent with microvesicles, and possibly more specifically, with exosomes.

In summary, it was found that PEG formulations containing PEG-10,000 and PEG-8,000 average molecular weights were most effective in isolating structures that exhibit the properties of microvesicles, and more specifically, exosomes, as demonstrated by Western blotting for known microvesicle markers, small RNA content, and NANOSIGHT® instrumentation for visualization and particle measurements.

Example 2

Isolation of Microvesicles from Urine and Western Blotting Verification

In this example, the ability of the a precipitation solution containing PEG-8,000 to precipitate and isolate microvesicles from human urine was tested, and the verified using western blotting using a known membrane marker.

Ten milliliters of normal human urine was combined with 2 ml PEG-8,000 precipitation solution, incubated for 16 hours at 4° C., and centrifuged at 1,500×g for 30 minutes. In some trials, a BECKMAN COULTER™ INC., Allegra™ 6R centrifuge with a swinging bucket rotor was used at a speed of 3,000 rpm producing 1,500×g relative centrifugal force. The resulting pellet was resuspended 175 uL PBS.

There are protein markers that are known to be abundantly associated with exosomes, including CD63, CD9, CD81 and Hsp70. The abundance of the CD9 protein marker in the resuspended pellet was analyzed by ELISA assay and Western blotting.

A) ELISA

Increasing amounts of the exosome suspension were loaded onto an ELISA-ready plate. The CD9 protein was detected using rabbit anti-CD9 primary antibody and an HRP-conjugated secondary goat anti-rabbit antibody (System Biosciences, Inc., ELISA Kit Catalog No. EXOEL-CD9A-1). See FIG. 2. The ELISA kit provides a set of standards calibrated using NANOSIGHT® instrumentation to quantitate the number of exosome particles present in a sample. The table below shows the standards in number of exosome particles and the corresponding exosome protein concentration (pg/mL). The standards values were graphed, and routinely displayed a linear curve, thereby permitting the assessment of number of exosomes or protein concentration (pg/mL) in an experimental sample with a correlation coefficient of $R^2=0.9812$ (where an $R^2$ value of 1 is an prefect standards correlation).

| Standard Tube | # Exosomes | Exosome protein [ ] |
|---|---|---|
| BLANK | 0 | — |
| 1 | $1.35 \times 10^{10}$ | 975 pg/ml |
| 2 | $6.75 \times 10^{9}$ | 488 pg/ml |
| 3 | $3.37 \times 10^{9}$ | 244 pg/ml |
| 4 | $1.68 \times 10^{9}$ | 122 pg/ml |
| 5 | $8.44 \times 10^{8}$ | 61 pg/ml |
| 6 | $4.21 \times 10^{8}$ | 30 pg/ml |
| 7 | $2.10 \times 10^{8}$ | 15 pg/ml |

B) Western Blotting

Figure 2:
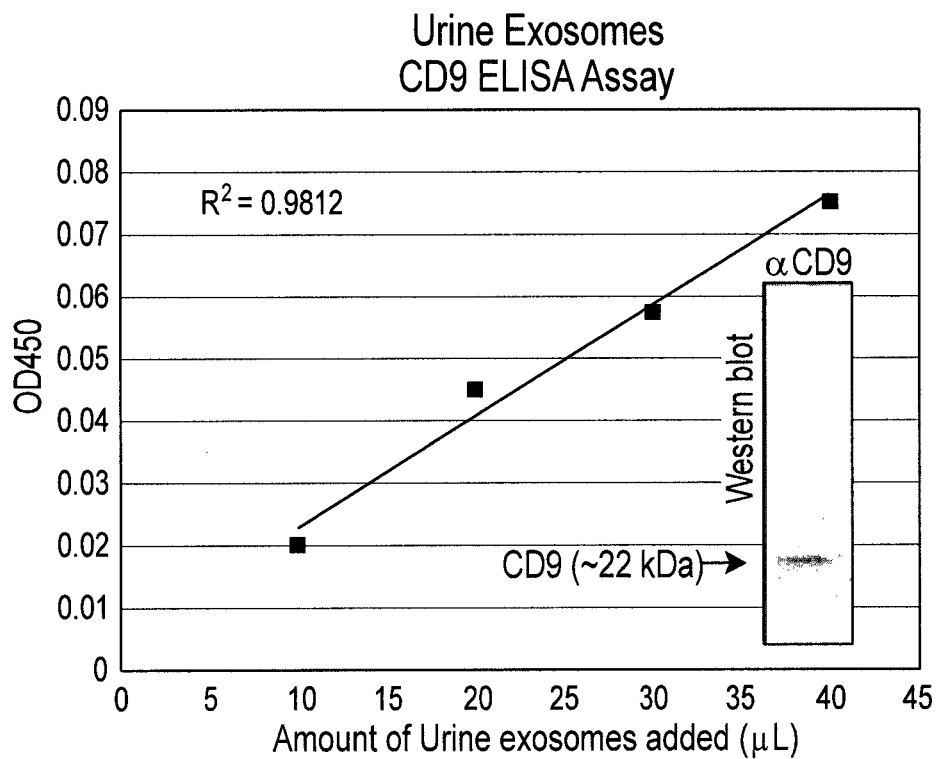
FIG. 2 provides the results of a Western blot analysis and an ELISA assay that examined the levels of CD9 protein in samples prepared from human urine.

The exosome suspension derived from urine was also used in a Western blot to detect the known exosome protein marker CD9 using the same set of antibodies as used in the ELISA. Samples were separated on gradient 4-15% PAGE gels, transferred to PVDF membranes and probed with anti-CD9 primary antibody, then probed with the secondary antibody, and subjected to color development. The results are shown in FIG. 2 in the insert. This Western blot reveals the abundant presence of an anti-CD9-reactive protein having the 22 kilodalton predicted molecular weight of the CD9 marker.

Example 3

Exosomes Isolation from Urine and Analysis by Electron Microscopy (EM)

In this example, the ability of a PEG-8,000 precipitation solution to precipitate and isolate microvesicles from human urine was tested, and then verified using EM visualization.

Human urine containing exosomes was centrifuged at 3000×g and 10,000×g for 15 minutes. The supernatant was filtered through a 0.22 μm filter. PEG-8,000 precipitation solution was added to the urine supernatants, and the mixture was refrigerated at 5° C. overnight. Following incubation, the mixture was centrifuged at 1500×g, and a pellet was resuspended 1:10 in sterile PBS.

Formvar/carbon-coated nickel grids were incubated on drops of 0.1% poly-L-lysine for 5 minutes, rinsed by water and dried. Freshly prepared grids were placed on top of exosome drops and incubated for 10 minutes to adsorb exosomes. The grids were washed on several drops of PBS and fixed with 2.5% glutaraldehyde in 0.1 M cacodylate buffer for 15 minutes.

After washing on several drops of water, exosomes were negatively stained: the grids were incubated on ice for 15 minutes, on 50 μl drops of the mixture of 2% methyl cellulose and 1% uranyl acetate (9:1). Excess contrasting mixture was removed and the grids were dried at room temperature before examination using an electron microscope.

Figure 3:
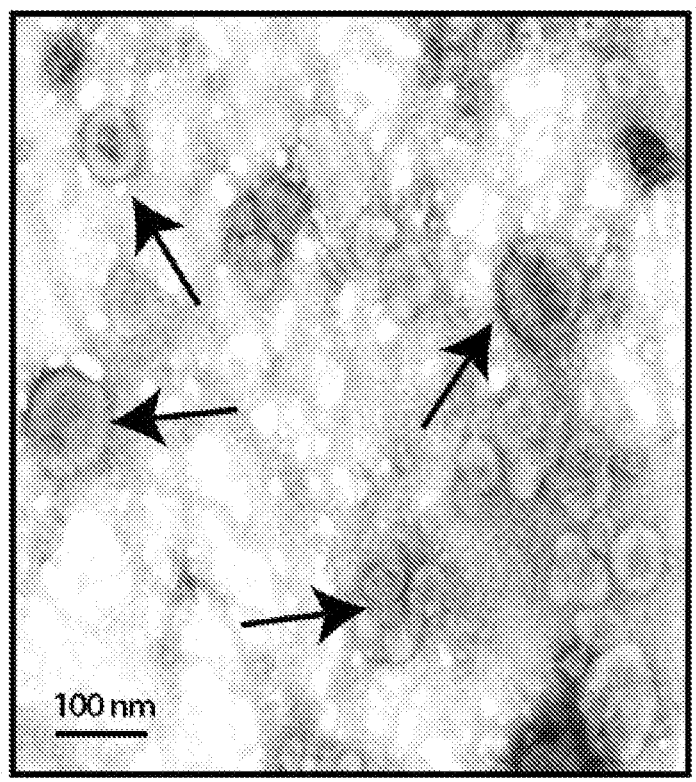
FIG. 3 provides an electron micrograph of a representative field from a sample of precipitated exosomes isolated from human urine. A size bar scale is shown on the bottom left.

The exosome microvesicles were visualized and photographed, a representative field is shown in FIG. 3. Arrows pointing to a few exosomes are indicated for reference. The exosomes isolated using the PEG-8,000 precipitation solution show the expected size distribution of 40-150 nm in diameter. Careful examination also shows the anticipated double-membrane structures of the exosome microvesicles. The size bar in the lower left corner designates 100 nm length.

Example 4

Comparisons with LifeTechnologies™ Reagents

The efficacy of precipitation solutions containing PEG-8,000 and PEG-10,000 were compared to the effectiveness of LifeTechnologies™ (Invitrogen™) ("LTI") Total Exosomes Isolation reagents intended for use with either conditioned cell culture media or serum.

Serum Exosome Isolation

Healthy human serum samples (500 uL) were used alternatively to isolate exosomes using the LifeTechnologies™ kit for total exosome isolation from serum (LifeTechnologies™ catalog no. 4478360) according to the manufacturer's recommended protocol, and a precipitation solution containing PEG-10,000 as per the description herein. Following the isolations, the number of exosomes isolated was measured using a System Biosciences, Inc. ELISA kit specific for protein marker CD63.

Figure 4A:
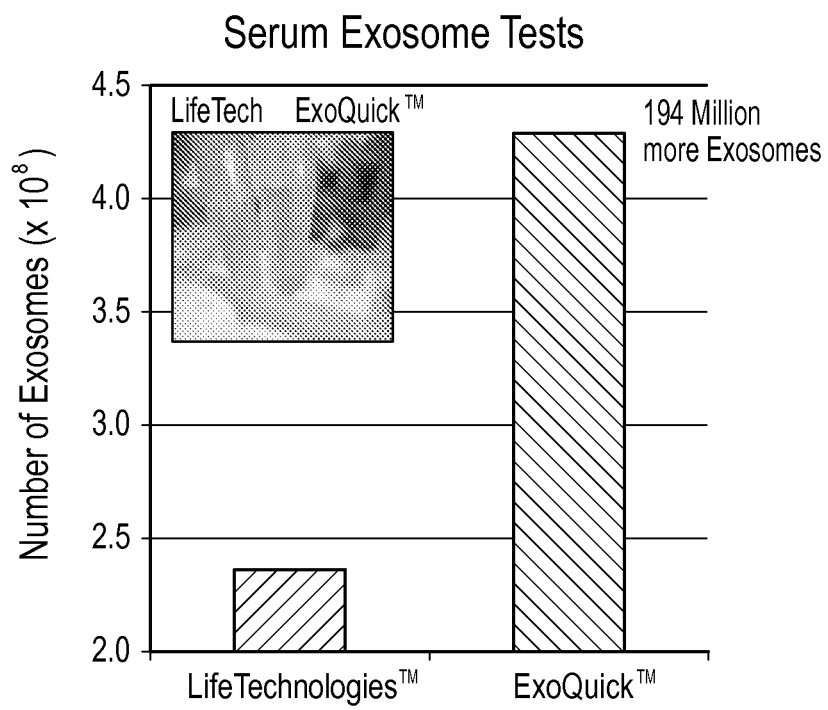
FIGS. 4A and 4B provide side-by-side comparisons of the ability of LifeTechnologies™ exosome precipitation reagents to isolate exosomes from serum compared to a PEG solution of the present invention (FIG. 4A) and to isolate exosomes from conditioned cell culture media compared to a PEG solution of the present invention (FIG. 4B).

As seen in FIG. 4A, the PEG-10,000 precipitation reagent precipitated significantly more exosomes compared to the LifeTechnologies™ product.

Conditioned Media Exosome Isolation

PC-3 prostate cancer cells were grown in a T75 flask in 20 ml DMEM supplemented with 10% fetal bovine serum (FBS), where the FBS supplement was previously depleted of exosomes (see Example 11). The cells were cultured for seven (7) days.

Exosome material was isolated from the conditioned cell culture media alternatively with either the LifeTechnologies™ kit for total exosome isolation from conditioned media (LifeTechnologies™ catalog no. 4478359) according to the manufacturer's recommended protocol, and a precipitation solution containing PEG-8,000 as per the description herein.

At the end of the seven days, exosomes were isolated. The number of exosomes isolated was measured by ELISA using an antibody specific for the CD63 protein marker (System Biosciences, Inc., ELISA Kit Catalog No. EXOEL-CD63A-

Figure 4B:
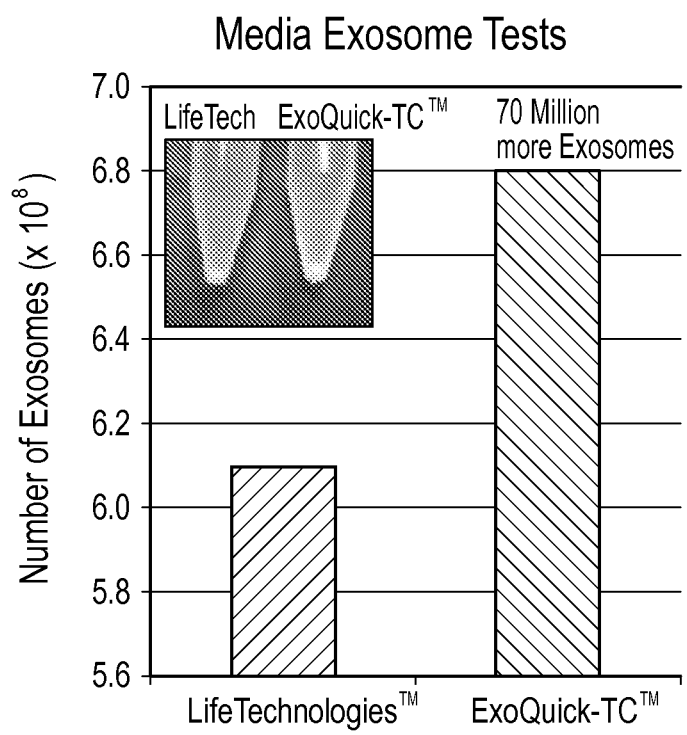

1). As seen in FIG. 4B, the PEG-8,000 precipitation reagent precipitated significantly more exosomes compared to the LifeTechnologies™ product.

In addition, another parallel cell culture was grown using minimal media supplemented with standard, untreated serum. It was further observed that there were no significant growth rate change or morphology differences between the cell cultures when comparing cultures that had been grown in the presence of cultured media supplemented with standard untreated FBS versus the exosome-depleted FBS supplements. This means that the exosome-depletion procedure using PEG-8,000 does not remove critical proteins/hormones or other signaling factors required for the healthy growth of PC-3 cells (FIG. 12A). We have also tested this on other cell lines and observed similar findings, e.g., with HT1080 cells (FIG. 12B).

Example 5

Exosome Isolation from Conditioned Media Derived from Cultured HT1080 Cells

In this example, the ability of the PEG-8,000 precipitation solution to precipitate and isolate microvesicles from conditioned cell culture media was tested using NANOSIGHT® instrumentation (NanoSight Ltd, Wiltshire, UK) for particle analysis and microscopic visualization.

Human HT1080 lung sarcoma cell line was cultured in serum-free media for 72 hours. Ten milliliters of the media was combined with 2 ml PEG-8,000 precipitation solution to pellet the exosomes overnight. The exosome pellet was resuspended in 1 ml PBS, diluted 1:40 and visualized on the NANOSIGHT® LM10 instrument. The NANOSIGHT® LM10 instrument is based on a conventional optical microscope and uses a laser light source to illuminate nano-scale particles within a 0.3 ml sample introduced to the viewing unit with a disposable syringe. Particles appear individually as point-scatterers moving under Brownian motion. The NANOSIGHT® image analysis software (Nanoparticle Tracking Analysis (NTA) software suite) determined microvesicle sizes on an individual basis. Results are displayed as a frequency size distribution graph and output to a spreadsheet. See Malloy, Carr and Wright, "Exosome and Microvesicle Characterization by Nanoparticle Tracking Analysis," a publication from NanoSight Limited, Wiltshire, United Kingdom, and "Applications of Nanoparticle Tracking Analysis (NTA) in Nanoparticle Research" a publication from NanoSight Limited, publication number M110B (2009) and Carr and Wright, "Nanoparticle Tracking Analysis: A Review of Applications and Usage 2010- 2012" a publication from NanoSight Ltd., publication number M0507 (2013).

Figure 5A:
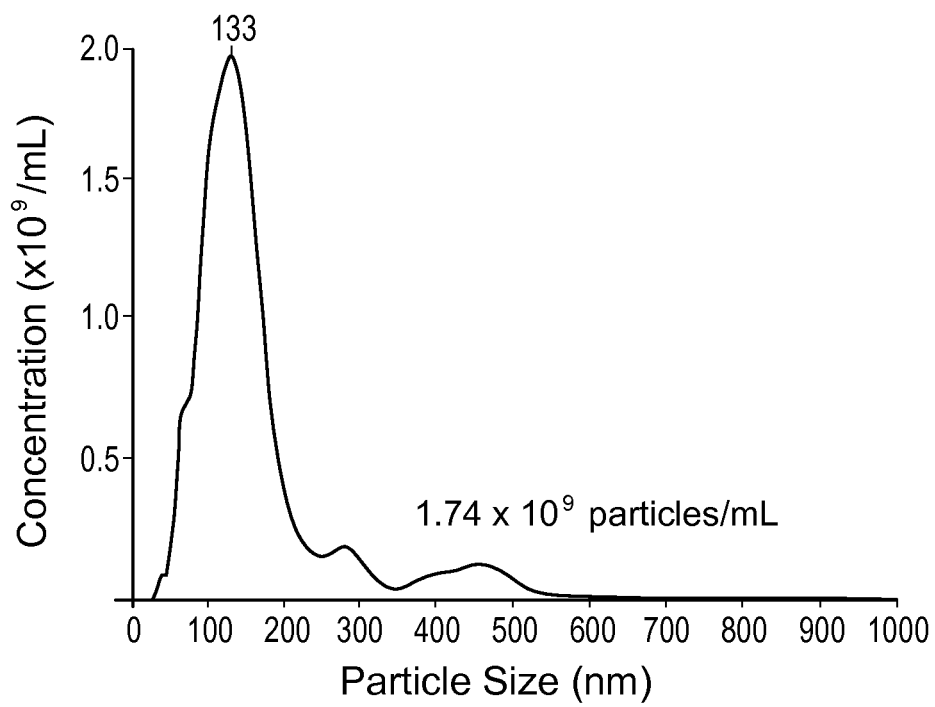
FIG. 5A provides a graphic showing the size distribution sorting analysis of microvesicles isolated from serum-free media used to culture the human HT1080 lung sarcoma cell line, as assessed using NANOSIGHT® instrumentation for nanoparticle tracking analysis (NTA).
Figure 5B:
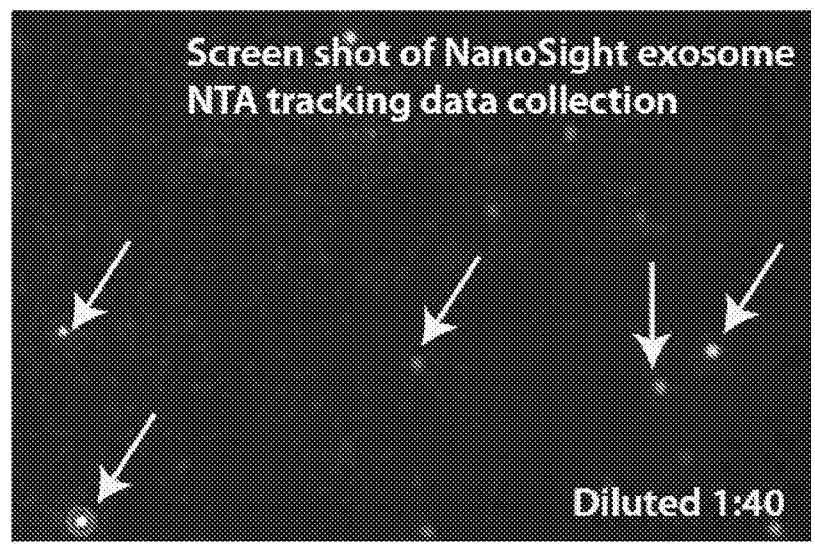
FIG. 5B provides an optical microsope representative field screen capture of the particles characterized in FIG. 5A using the NANOSIGHT® LM10 instrumentation. Exosome particles are indicated by arrows.

The NANOSIGHT® sorting analysis (FIG. 5A) shows that PEG-8,000 precipitation solution isolated exosomes having an average diameter of approximately 133 nm, with a recovery of $1.74 \times 10^9$ particles/ml. FIG. 5B shows a screen shot of NANOSIGHT® exosome NTA tracking data collection using the NANOSIGHT® LM10 instrument, with the exosome particles indicated by arrows.

Example 6

Exosome Isolation from Conditioned Media Derived from Cultured HEK293 Cells

In this example, the ability of the PEG-8,000 precipitation solution to precipitate and isolate microvesicles from conditioned cell culture media was tested, and then verified using NANOSIGHT® instrumentation and microscopic visualization screen shots.

Figure 6A:
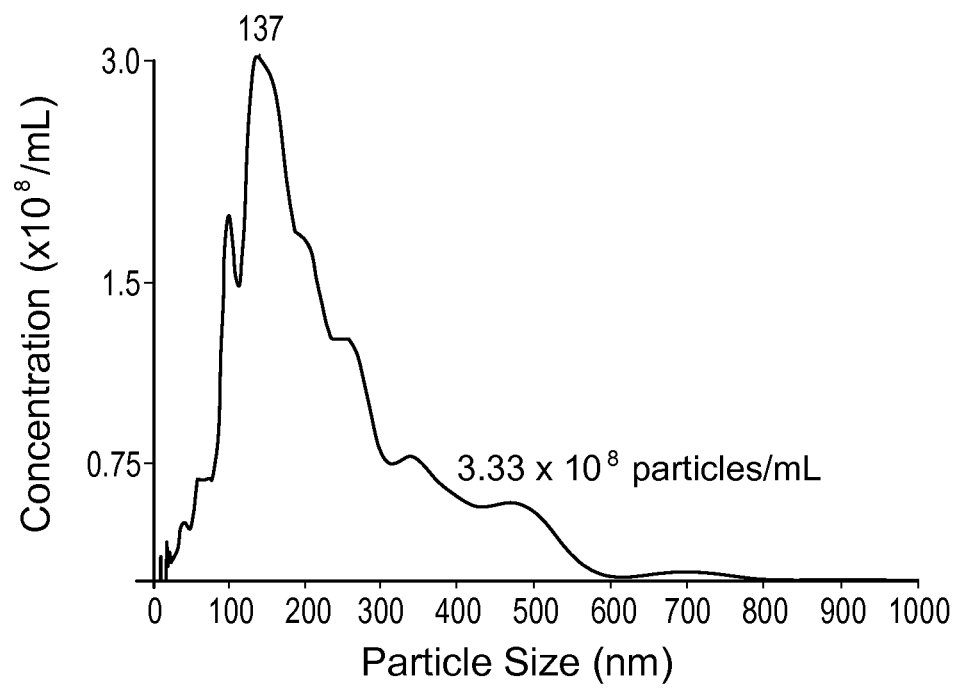
FIG. 6A provides a graphic showing the size distribution sorting analysis of microvesicles isolated from serum-free media used to culture the human embryonic kidney (HEK) cell line, as assessed using NANOSIGHT® instrumentation for nanoparticle tracking analysis (NTA).
Figure 6B:
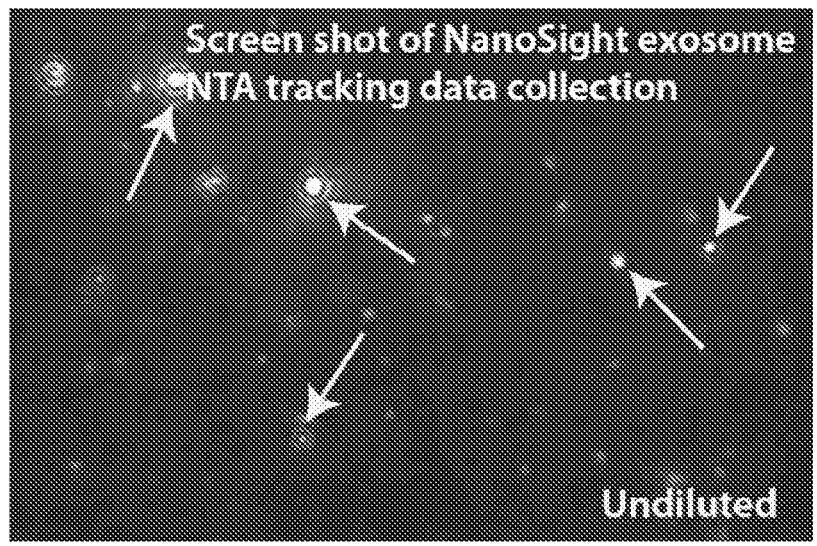
FIG. 6B provides an optical microscope representative field screen capture of the particles characterized in FIG. 6A using the NANOSIGHT® LM10 instrumentation. Exosome particles are indicated by arrows.

Human embryonic kidney (HEK) cell line was cultured in conditioned media (serum-free) for 72 hours. Ten milliliters of the media was combined with 2 ml PEG-8,000 precipitation solution to pellet to pellet the exosomes overnight. The exosome pellet was resuspended in 1 ml PBS and visualized on the NANOSIGHT® LM10 instrument undiluted. The analysis in FIG. 6A shows that PEG-8,000 precipitation solution to pellet isolated 137 nm exosomes with a recovery of $3.33 \times 10^8$ particles/ml. FIG. 6B shows a screenshot capture of the exosome particles observed during the NTA analysis, with the exosome particles indicated by arrows.

Example 7

Exosome Isolation from Human Urine

In this example, the ability of PEG-8,000 precipitation solution to precipitate and isolate microvesicles from human urine was tested, and then verified using NANOSIGHT® instrumentation and microscopic visualization screen shots.

Figure 7A:
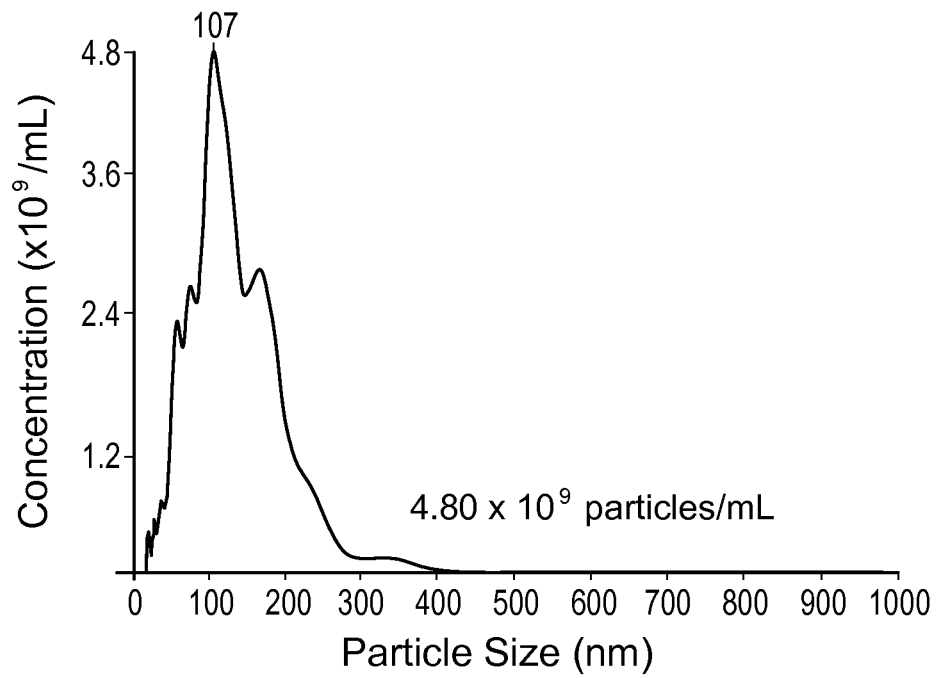
FIG. 7A provides a graphic showing the size distribution sorting analysis of microvesicles isolated from urine, as assessed using NANOSIGHT® instrumentation for nanoparticle tracking analysis (NTA).
Figure 7B:
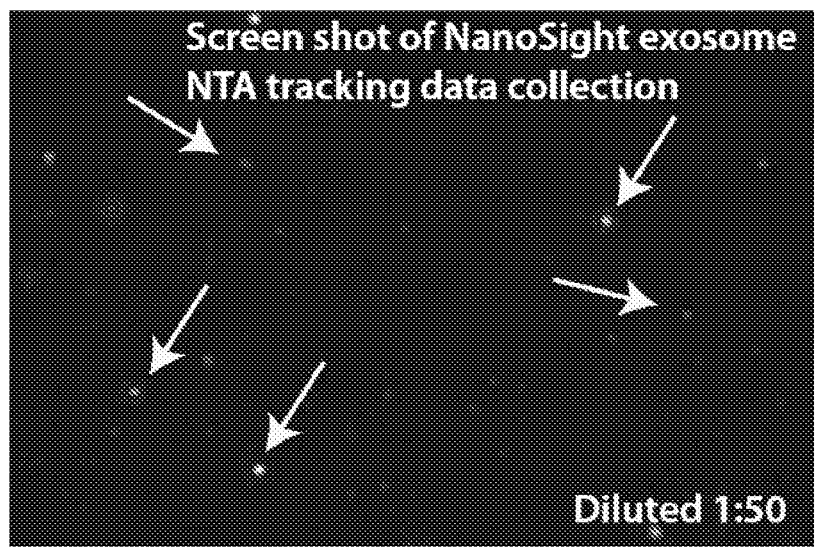
FIG. 7B provides an optical microscope representative field screen capture of the particles characterized in FIG. 7A using the NANOSIGHT® LM10 instrumentation. Exosome particles are indicated by arrows.

A five milliliter sample of normal human urine was combined with either 1.0 mL or 2.5 mL of the PEG-8,000 precipitation solution to pellet the exosomes overnight. The exosome pellet was resuspended in one milliliter PBS, diluted 1:50 and the microparticles were characterized using NANOSIGHT® instrumentation. See FIG. 7A. The analysis shows that PEG-8,000 precipitation solution isolated exosomes having an average size of 107 nm in diameter and with a recovery of $4.80 \times 10^9$ particles/ml. FIG. 7B shows a screenshot capture of the exosome particles observed during the NTA analysis, with the exosome particles indicated by arrows.

Example 8

Scanning EM of Exosomes Isolated Using PEG-8,000

Figure 8:
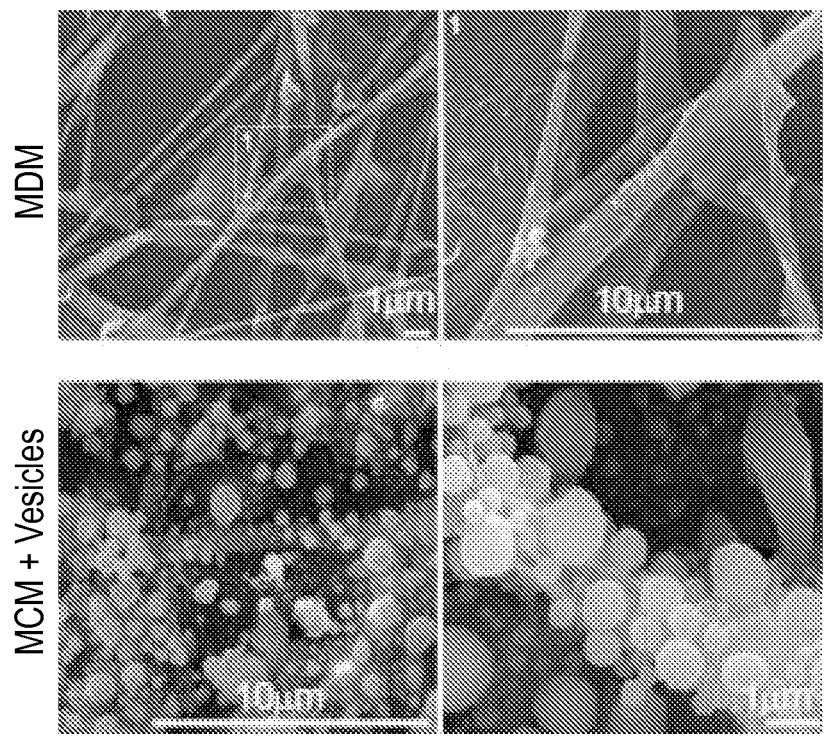
FIG. 8 provides a scanning electron micrograph of microvesicles adhering to the cell membrane surface of monocyte-derived macrophage (MDM) cells. Size bar scales are shown in each panel.

In this example, the size and structure of exosome vesicles are visualized by scanning electron microscopy. These images are shown in FIG. 8.

Monocyte-derived macrophage (MDM) cells were seeded on a filter membrane prior to and after migration toward the enriched vesicles in a Boyden chemotaxis chamber (scale bar, 1 um; expanded box, 10 um) and then imaged using scanning electron microscopy. Exosome membranes demonstrated a high affinity for the surface of the target MDM cells, and their adhesion to the plasma membrane was resistant to washes. These data are adapted from Kadiu et al., "Biochemical and Biologic Characterization of Exosomes and Microvesicles as Facilitators of HIV-1 Infection in Macrophages," J. Immunol. (ePub Jun. 18, 2012).

Example 9

Verification of Isolated Microvesicles by Protein Analysis

In this example, microvesicles isolated using System Biosciences, Inc., ExoQuick™ (comprising PEG 10,000) by the methods of the invention were analyzed for the presence of marker proteins by Western blotting.

A) Confirmation of Exosome Isolation by Protein Marker Analysis

Common protein markers for microvesicles were assayed by Western blotting in isolated microvesicle preparations prepared using the PEG precipitation methods of the invention.

Normal human serum samples (500 uL) were used. The Western analysis gel used 40 µg of precipitated exosome protein loaded per well for SDS-PAGE separation. The gel was transferred to nitrocellulose and probed with either anti-CD9 primary antibody (R&D SYSTEMS® catalog no. MAB1880 rabbit anti-Human CD9 MAb Clone 209306, Mouse IgG2B) or anti-CD63 primary antibody (R&D SYSTEMS® catalog no. MAB5048, rabbit anti-Human CD63 MAb Clone 460305, Mouse IgG1). The primary antibodies used were used at a 1:1,000 dilution. The primary antibodies were visualized with goat anti-rabbit HRP secondary antibody (THERMO FISHER SCIENTIFIC™ catalog no. 31460, goat anti-rabbit IgG (H+L), peroxidase conjugated secondary antibody) at a 1:20,000 dilution. The signals were developed using SuperSignal West Femto substrate kit (THERMO FISHER SCIENTIFIC™ catalog no. 34094).

Figure 14A:
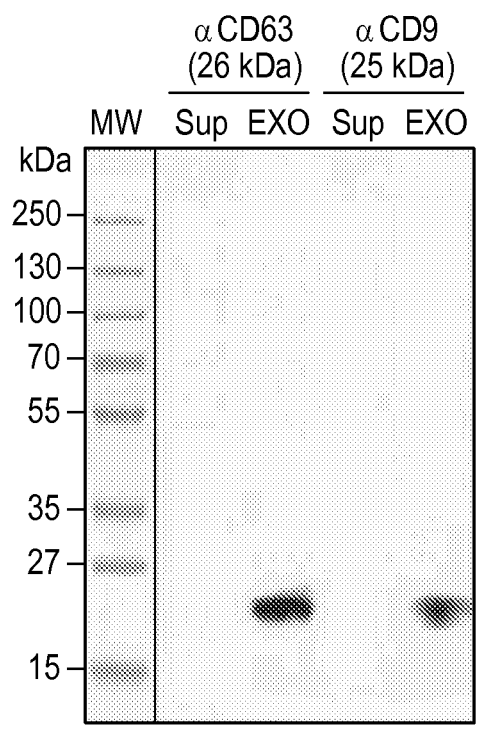
FIG. 14A provides a Western blot analysis verifying the presence of known exosome markers CD9 and CD63 in exosome samples isolated from normal human serum using ExoQuick™ (comprising PEG 10,000).

This Western blot is shown in FIG. 14A. This blot verifies that the pellet material following centrifugation contains exosome-specific markers CD63 and CD9, but those same markers are absent from the serum supernatant.

Figure 14B:
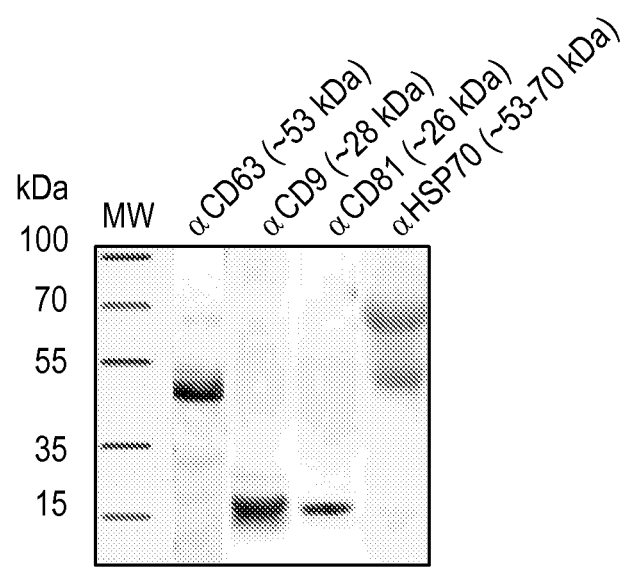
FIG. 14B provides a Western blot analysis verifying the presence of known exosome markers CD9, CD63, CD81 and Hsp70 in exosome samples isolated from normal human serum using ExoQuick™ (comprising PEG 10,000).

FIG. 14B provides Western blot data verifying the presence of known exosome markers CD9, CD63, CD81 and Hsp70 in exosome samples isolated from normal human serum using System Biosciences, Inc., ExoQuick™ (comprising PEG 10,000). The exosome markers were detected using four primary antibodies and reagents from the System Biosciences, Inc. Exosome Sampler Kit (catalog no. EXOAB-KIT-1) and visualized with goat anti-rabbit HRP secondary antibody (THERMO FISHER SCIENTIFIC™ catalog no. 31460, goat anti-rabbit IgG (H+L), peroxidase conjugated secondary antibody) at a 1:20,000 dilution. The signals were developed using SuperSignal West Femto substrate kit (THERMO FISHER SCIENTIFIC™ catalog no. 34094).

This Western blot is shown in FIG. 14B. This blot verifies that the pellet material following centrifugation contains exosome-specific markers CD9, CD63, CD81 and Hsp70.

B) Comparison of Exosome Isolation Techniques by Protein Marker Analysis

Several methods have been developed for isolating exosomes and EMVs in biological samples. The most common method, ultracentrifugation, requires long process times and expensive equipment. Other commercial methods rely on antibodies or filtration approaches, neither of which are not well characterized. As described herein, exosomes can be isolated using polyethylene glycol (PEG) polymer formulations, as demonstrated by known exosome markers in Western blots, ELISAs, physical dimensions such as diameters measured using electron microscopy and NANOSIGHT® particle analysis methods. Exosomes isolated by the protocols described herein also contain exosome RNA cargo.

The number of microvesicles/exosomes recovered from urine using side-by-side comparison of various methodologies was assessed. Exosomes recovered from the urine samples using the various methods was quantified using CD9 enzyme-linked immunosorbent assay (ELISA). The various isolation methods employed to isolate the exosomes were as follows:

| Protocol Number | Methodology | Yield (CD9 positive exosomes per x) |
|---|---|---|
| P1 | Ultracentrifugation | $1.5 \times 10^9$ particles |
| P2 | Ultracentrifugation + 30% sucrose cushion | $2.5 \times 10^8$ particles |
| P3 | Ultracentrifugation + 0.22 mm filtration | $3.5 \times 10^8$ particles |
| P4 | Nanomembrane ultrafiltration concentrator (SARTORIOUS Vivaspin ® 20) | $1.2 \times 10^9$ particles |
| P6 | Exosome precipitation using PEG-8,000 | $2.7 \times 10^9$ particles |

Figure 15:
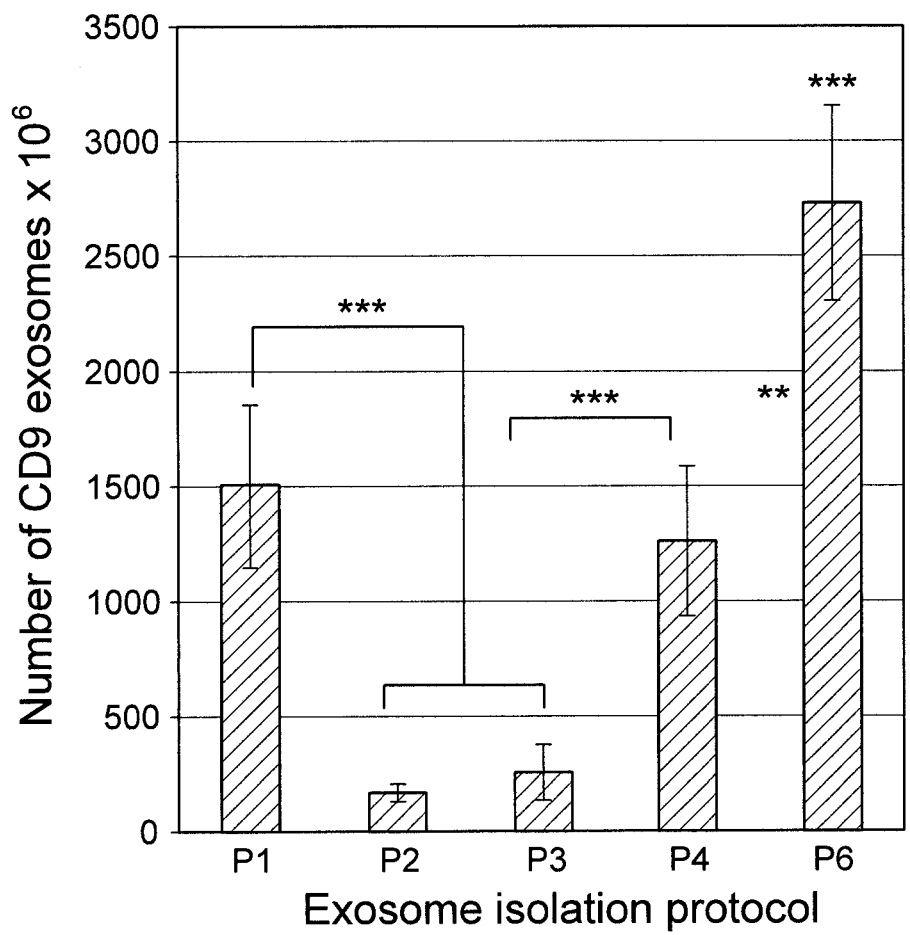
FIG. 15 provides a histogram showing side-by-side testing data to assess and compare the efficacy of various methods for microvesicle isolation from urine samples.

As shown in FIG. 15, the highest number of exosome particles isolated per milliliter of urine was obtained using method P6, which was the PEG-8,000 precipitation method according to the protocols of the present invention. That method yielded approximately $2.7 \times 10^9$ CD9-positive exosomes per mL of urine, as determined using an anti-CD9 enzyme-linked immunosorbent assay (ELISA). It was observed that the yield of exosome particles per milliliter of urine using the PEG-8,000 precipitation method of the present invention was more than five times higher compared to the lowest yield of exosome particles using an ultracentrifugation protocol (P2). The brackets group samples having significant differences and the asterisks refer to $P<0.01$ and *$P<0.001$ values.

Data and figure adapted from Alvarez et al., "Comparison of protein, microRNA, and mRNA yields using different methods of urinary exosome isolation for the discovery of kidney disease biomarkers," *Kidney Int.* (Jul. 11, 2012); doi: 10.1038/ki.2012.256.

Example 10

Enrichment of Small RNAs in the Microvesicle Pellet Fraction

A characteristic feature of exosome microvesicles is that they contain small RNAs encapsulated in the vesicle. Exosomes isolated from human urine as described in Example 2 were lysed using Trizol reagents and the RNA extracted using standard methods. The RNA was separated on a 15% TBE-Urea gel and visualized using SYBR green staining for RNA.

Figure 9:
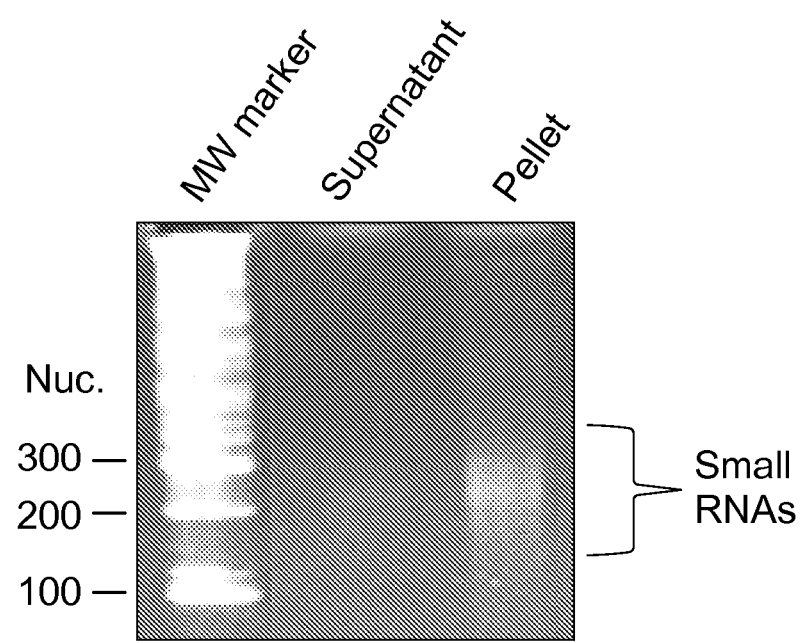
FIG. 9 provides a photographic image of a 15% TBE-urea gel visualized using SYBR green staining for RNA. The supernatant and pellet samples are taken following exosome isolation from a human urine sample.

RNA enrichment was compared between the supernatant and the exosome pellet. The data shown in FIG. 9 reveals a nearly quantitative enrichment of small RNAs from the exosomes isolated using the PEG-8,000 precipitation method of the invention.

This is further evidence that microvesicles are segregating in the pellet fraction in the methods of the present invention.

Example 11

Production of Microvesicle-Depleted Blood Serum for Use in Cell Culture Media

Bovine exosomes are present in standard FBS media supplements. These endogenous exosomes can interfere with experimental results and data interpretation, and will co-purify with exosomes that are produced by the cultured cell line of interest. This example describes a protocol for the removal of endogenous microvesicles from serum, and further, demonstrates that the exosome-stripped serum retains its growth supplement properties after undergoing the exosome stripping process.

Standard FBS was thawed from frozen and mixed by inversion. 200 ml of the FBS was transferred to a sterile 250 mL screw cap conical bottom centrifuge tube (Corning, catalog no. 430776).

To this tube was added 40 ml of PEG-10,000 precipitation solution and mixed by inversion five times. The mixture was placed at 4° C. for 2 hours. The mixture may become slightly cloudy.

Following the incubation, the mixture was centrifuged at 1,500×g (3,000 rpm Beckman GS6R swinging bucket rotor) for 30 minutes at 4° C. At the completion of the spin, there appeared a white-beige pellet at the bottom of the centrifuge bottle. The FBS supernatant was carefully removed, leaving behind about 3 ml of supernatant on top of the exosome pellet. The supernatant was transferred to fresh, sterile bottles for filtration and packaging.

Example 12

Exosome-Depleted Serum Contains Reduced Particles Compared to Untreated Serum

The exosome-depleted serum described in Example 11 was analyzed for the presence of exosome particles using NANOSIGHT® particle analysis. The original untreated serum was also analyzed in parallel.

Figure 10:
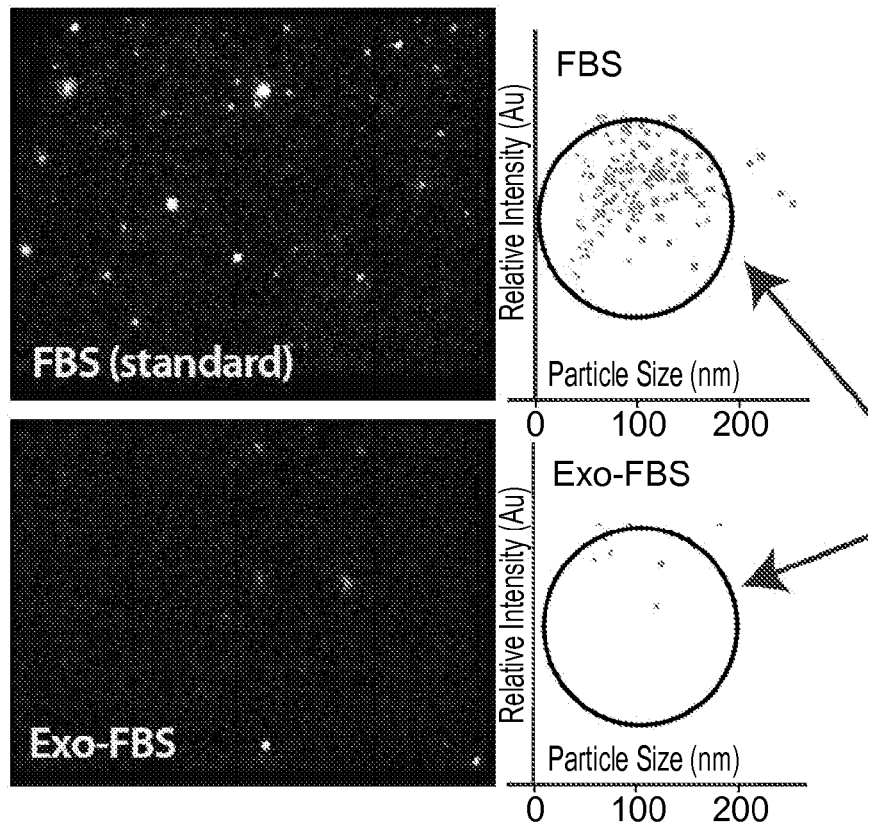
FIG. 10 provides microparticle sorting analyses and microscope field of view captures of standard FBS (top two panels) and FBS that has been depleted of microparticles using a PEG-10,000 precipitation solution (bottom two panels).

The results are shown in FIG. 10. As can be seen in the figure, the stripped FBS (bottom panel) is characterized by a vast reduction in the number of particles compared to the untreated serum (top panel), as seen in both the particle sorting and microscope field of view.

Example 13

Exosome-Depleted Serum is Devoid of Detectable Bovine CD63 Protein

The exosome-depleted serum described in Example 11 was analyzed for the presence of bovine CD63 protein, as measured by ELISA. The original untreated serum was also analyzed in parallel.

Figure 11:
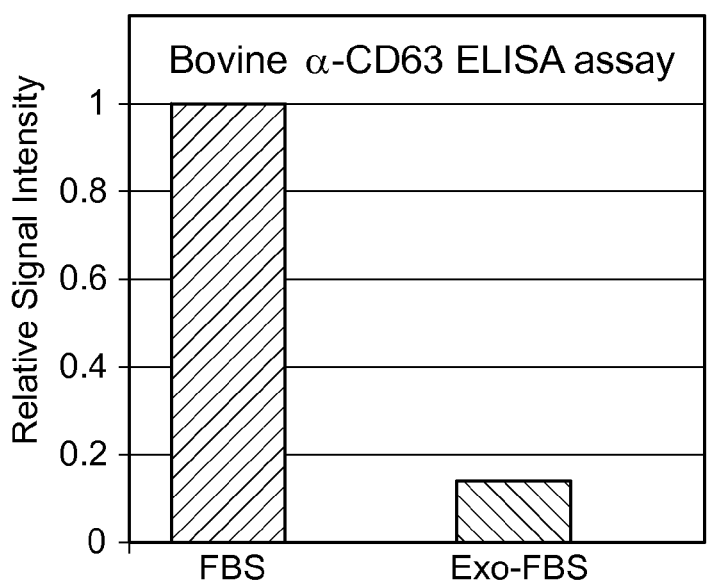
FIG. 11 provides a histogram showing ELISA results measuring the presence of bovine CD63 protein in untreated serum (FBS) and exosome-depleted serum (Exo-FBS).

Equal volumes (50 ul) of either standard (untreated) FBS or exosome-depleted media supplement were used in the ELISA assay. These results are shown in FIG. 11. The quantity of CD63 signal intensity is normalized to an arbitrary value of 1.0 in the untreated FBS sample. As can be clearly seen in the figure, there is a marked reduction (approximately 10 fold) in the level of anti-CD63 binding activity in the exosome-depleted serum sample compared to the untreated FBS sample, resulting in a loss of a majority of the exosomes originally contained in the FBS.

Example 14

Exosome-Depleted Serum Supports Robust Cell Growth

The exosome-depleted serum (Exo-FBS) described in Example 11 was analyzed for its ability to support cell growth in culture, as compared to untreated fetal bovine serum (FBS). Complete medium was made from DMEM media supplemented with either 10% standard FBS or with 10% exosome-depleted FBS. HT1080 fibrosarcoma cells and HEK293 cells were cultured under standard conditions at 37° C. with 5% $CO_2$ for 5 days in the two different DMEM media indicated.

Figure 12:
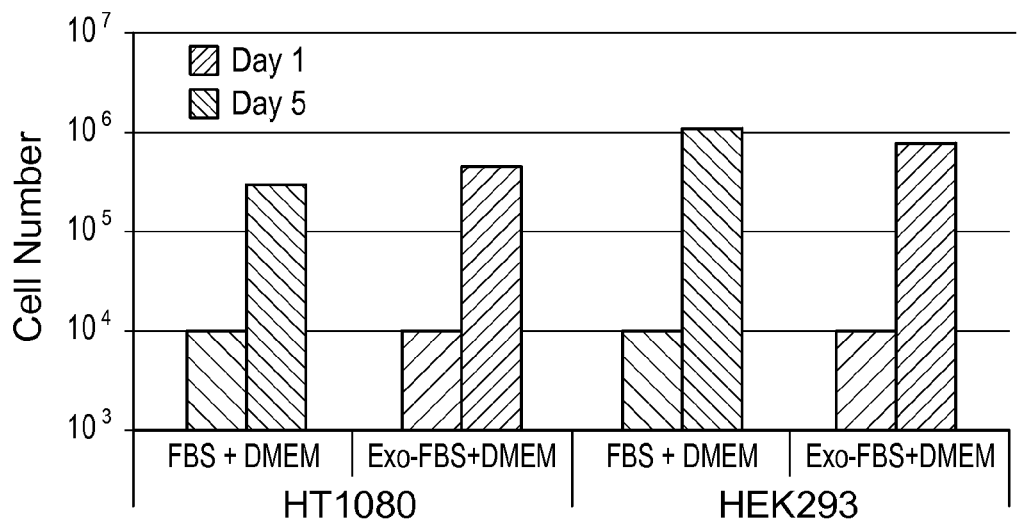
FIG. 12 provides a histogram summarizing comparative cell growth data for the cell lines, where each of those lines was alternatively cultured in DMEM supplemented with either untreated fetal bovine serum (FBS) or exosome-depleted serum (Exo-FBS).

After this culture period, the cell numbers in the cultures were determined using a hemocytometer (FIG. 12). As observed in FIG. 12, there was no significant quantitative difference between FBS and the exosome-depleted FBS to support cell growth as measured by cell numbers.

Figure 13A:
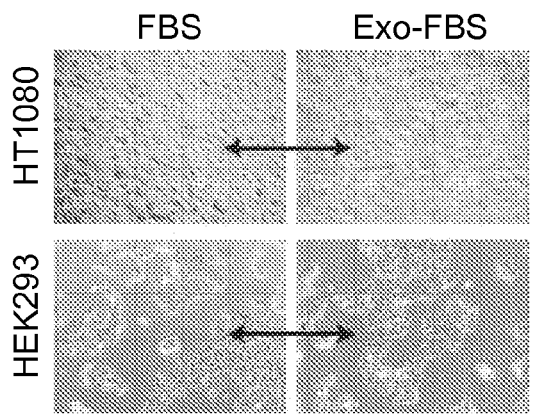
FIG. 13A provides phase-contrast light microscope images of HT1080 and HEK293 cell cultures that were alternatively cultured in DMEM supplemented with either untreated fetal bovine serum (FBS) or exosome-depleted serum (Exo-FBS).
Figure 13B:
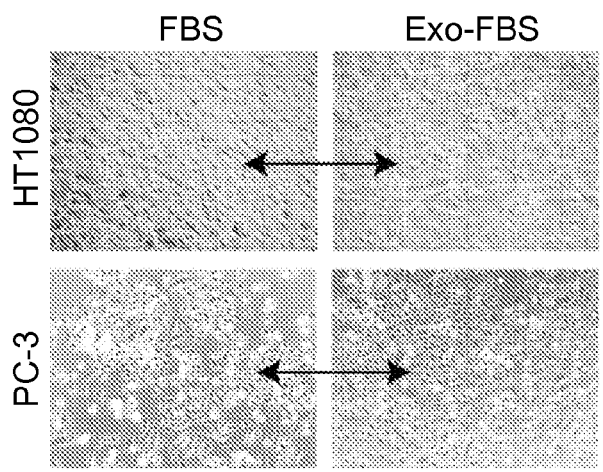
FIG. 13B provides phase-contrast light microscope images of HT1080 and PC-3 cell cultures that were alternatively cultured in DMEM supplemented with either untreated fetal bovine serum (FBS) or exosome-depleted serum (Exo-FBS).

After this same culture period, the cultures were examined under a light microscope to characterize growth morphology (FIGS. 13A and 13B). Similar to the cell number analysis, there were no obvious phenotypic differences between three different cell type cultures when grown alternatively in either FBS or the exosome-depleted FBS.

Collectively, these results indicate that the exosome depletion method of the present invention does not produce serum that is deficient in its ability to support cell grow in culture.

Example 15

Bovine microRNAs Present in Untreated FBS are Undetectable or Reduced in Exosome-Depleted FBS The exosome-depleted serum described in Example 11 was analyzed for its RNA content. Standard FBS and exosome-depleted-FBS media supplements (4 mL each) were treated with Trizol extraction methods to recover exosome RNAs. The extracted RNA was resuspended in 20 μL water.

RNA (5 μL input) was used to generate cDNA, and 72 individual bovine microRNAs were measured by qPCR using the System Biosciences, Inc. (Mountain View, Calif.) QuantiMir system. The abundance level of a transcript as measured by quantitative PCR (qPCR) is indicated by cycle threshold (Ct) values. These Ct values are then normalized to a negative control measurement of Ct=40 and the delta delta Ct (DDCt) number is used to graph the results on the y-axis. The standard method equation for this calculation is: $DDCt=2^{\wedge}-(target-control)$.

Figure 16A:
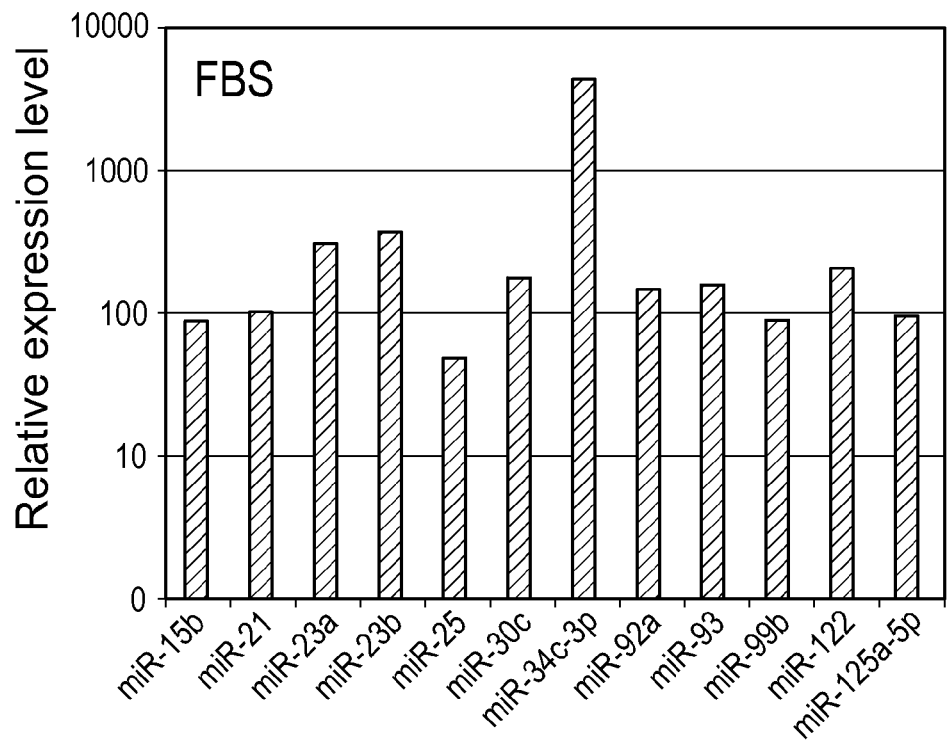
FIGS. 16A and 16B provide graphic summaries of qPCR testing for the presence and relative abundances of 12 RNA sequences.
Figure 16B:
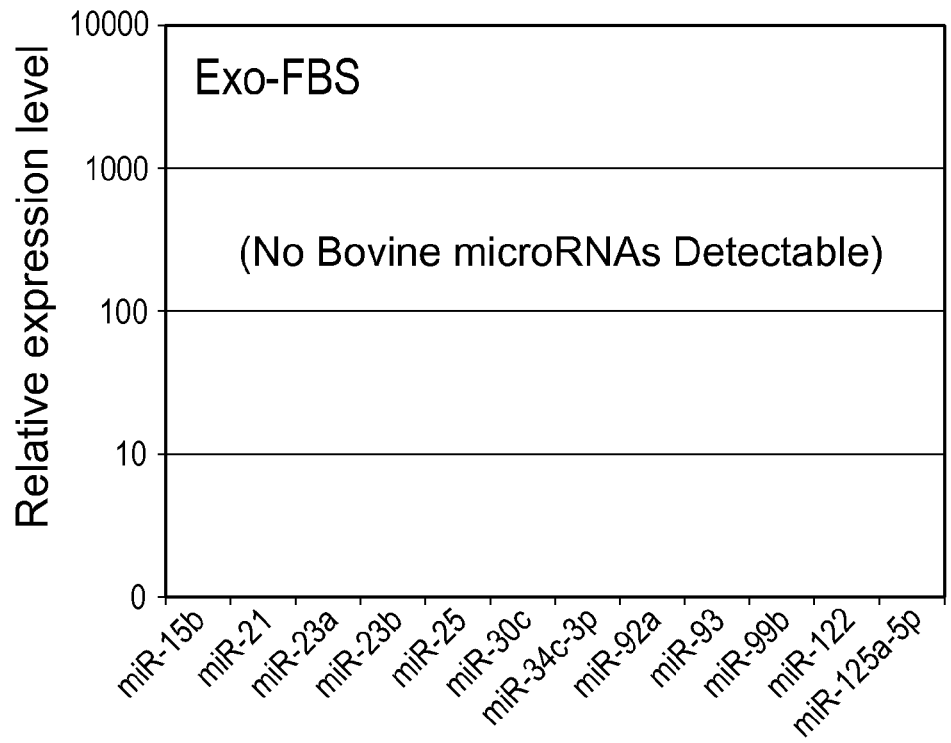

Of the 72 microRNAs tested, 12 yielded amplification curves in the FBS sample, as shown graphically in FIG. 16A, but not in the exosome-depleted-FBS sample, as shown graphically in FIG. 16B. Results are also shown in the table below. As can be clearly seen, bovine microRNAs present in untreated FBS are either not detectable or significantly diminished in the exosome-depleted FBS generated by the method of Example 11 for each of the 12 transcripts tested.

| miR | Ct | FBS Exp Level |
|---|---|---|
| hsa/bta-miR-15b | 33.57 | 86.48 |
| hsa/bta-miR-21 | 33.30 | 103.95 |
| hsa/bta-miR-23a | 31.72 | 310.93 |
| hsa/bta-miR-23b | 31.46 | 372.24 |
| hsa/bta-miR-25 | 34.40 | 48.51 |
| hsa/bta-miR-30c | 32.53 | 177.65 |
| hsa/bta-miR-34c-3p | 27.88 | 4447.08 |
| hsa/bta-miR-92a | 32.81 | 146.34 |
| hsa/bta-miR-93 | 32.69 | 158.72 |
| hsa/bta-miR-99b | 33.51 | 89.63 |
| hsa/bta-miR-122 | 32.32 | 205.57 |
| hsa/bta-miR-125a-5p | 33.43 | 95.19 |

\* \* \*

While the foregoing invention has been described in some detail for purposes of clarity and understanding, it will be clear to one skilled in the art from a reading of this disclosure that various changes in form and detail can be made without departing from the true scope of the invention. It is to be understood that the invention is not limited to any of the specifically recited methodologies or materials such as reagents, equipment or biological materials recited herein. Similar or equivalent methodologies and materials can be used in the construction and practice of the present invention, and remain within the scope of the invention. It is also understood that the description and terminology used herein is for the purpose of describing particular embodiments of the invention only, and is not intended that the invention be limited solely to the embodiments described herein.

As used in this specification and the appended claims, singular forms such as "a", "an" and "the" include plural referents unless the content clearly dictates otherwise. For example, reference to "a microvesicle" or "an exosome" also includes a plurality of microvesicles or a plurality of exosomes. All industry and technical terms used herein have the same meaning consistent with and commonly understood by one of ordinary skill in the art or industry to which the invention pertains, unless defined otherwise.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for isolating cell secreted microvesicles from a liquid sample, the method comprising:
   a) providing:
      i) a liquid sample, and
      ii) a precipitation solution comprising at least one species of polyethylene glycol (PEG) having a molecular weight of between and including 400 and 8,000 Daltons;
   b) combining the precipitation solution with the liquid sample to form an admixture;
   c) incubating the admixture;
   d) centrifuging the admixture to form a pellet and a supernatant;
   e) removing said supernatant; and
   f) resuspending said pellet in a resuspension solution, thereby isolating cell secreted microvesicles from the liquid sample.

2. The method of claim 1, wherein the isolated cell secreted microvesicles comprise exosomes.

3. The method of claim 1, wherein the liquid sample comprises conditioned cell culture media.

4. The method of claim 1, wherein the liquid sample comprises a biofluid.

5. The method of claim 1, wherein the liquid sample comprises a fluid selected from the group consisting of whole blood, blood serum, blood plasma, urine, saliva, sputum, breast milk, ascites fluid, synovial fluid, amniotic fluid, semen, cerebrospinal fluid, follicular fluid and tears.

6. The method of claim 1, wherein the PEG in said precipitation solution is in a weight concentration range of about 300 milligrams per milliliter (mg/mL) to about 500 mg/mL.

7. The method of claim 1, wherein the PEG in said precipitation solution is in a weight concentration of about 500 mg/mL.

8. The method of claim 1, wherein the centrifuging step comprises subjecting the admixture to a centrifugal force that does not exceed about 10,000×g.

9. The method of claim 1, wherein the centrifuging step comprises subjecting the admixture to a centrifugal force of about 1,500×g.

10. The method of claim 1, wherein the liquid sample and the precipitation solution are combined in a volume ratio of about 5:1.

11. The method of claim 1, wherein resuspending the pellet comprises resuspending the pellet in a volume of resuspension solution that is less than the starting volume of the liquid sample.

12. The method of claim 1, wherein the resuspension solution comprising the resuspended pellet is enriched for at least one marker known to correlate with exosomes.

13. The method of claim 12, wherein the at least one marker is either a protein marker or a nucleic acid marker.

14. The method of claim 1, wherein the isolated cell secreted microvesicles comprises a population of secreted microvesicles whose average diameter is between about 40 nm and about 150 nm.

15. A method for producing a microvesicle-depleted serum that is at least partially depleted of secreted microvesicles, the method comprising:
   a) providing:
      i) a serum, and
      ii) a precipitation solution comprising at least one species of polyethylene glycol (PEG) having a molecular weight of between and including 400 and 8,000 Daltons;
   b) combining the precipitation solution with the serum to form an admixture;
   c) incubating the admixture;
   d) centrifuging the admixture to form a pellet and a supernatant; and
   e) recovering the supernatant to a suitable container, thereby producing a serum that is at least partially depleted of secreted microvesicles.

16. The method of claim 15, wherein the microvesicle-depleted serum comprises secreted microvesicles in a concentration of not more than about $10^4$ microvesicles per milliliter (mL).

17. The method of claim 15, wherein the serum is selected from a bovine serum, a horse serum, a human serum, a rat serum, a mouse serum, a rabbit serum, a sheep serum, a goat serum, a lamb serum, a chicken serum and a porcine serum.

18. The method of claim 15, wherein the serum is a fetal bovine serum.

19. The method of claim 15, wherein the PEG in said precipitation solution is in a weight concentration range of about 300 milligrams per milliliter (mg/mL) to about 500 mg/mL.

20. The method of claim 15, wherein the PEG in said precipitation solution is in a concentration of about 500 mg/mL.

21. The method of claim 15, wherein the serum and the precipitation solution are admixed in a volume ratio of about 5:1.

22. The method of claim 15, wherein the centrifuging step comprises subjecting the admixture to a centrifugal force that does not exceed about 10,000×g.

23. The method of claim 15, wherein the centrifuging step comprises subjecting the admixture to a centrifugal force of about 1,500×g.

* * * * *